(12) United States Patent
Hibino et al.

(10) Patent No.: US 8,906,629 B2
(45) Date of Patent: Dec. 9, 2014

(54) METHOD FOR SCREENING AMELIORANTS OF DRY SKIN CAUSED BY ATOPIC DERMATITIS USING BLEOMYCIN HYDROLASE ACTIVITY AS INDICATOR

(75) Inventors: Toshihiko Hibino, Yokohama (JP); Yayoi Kamata, Yokohama (JP); Mami Yamamoto, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 12 days.

(21) Appl. No.: 13/513,537

(22) PCT Filed: Dec. 2, 2010

(86) PCT No.: PCT/JP2010/071599
§ 371 (c)(1),
(2), (4) Date: Jun. 1, 2012

(87) PCT Pub. No.: WO2011/068166
PCT Pub. Date: Jun. 9, 2011

(65) Prior Publication Data
US 2012/0302649 A1    Nov. 29, 2012

(30) Foreign Application Priority Data
Dec. 3, 2009   (JP) ................................ 2009-275909

(51) Int. Cl.
| | | |
|---|---|---|
| *C12Q 1/68* | (2006.01) | |
| *C12Q 1/34* | (2006.01) | |
| *G01N 33/68* | (2006.01) | |
| *C12Q 1/37* | (2006.01) | |

(52) U.S. Cl.
CPC ...... *G01N 33/6881* (2013.01); *G01N 2800/202* (2013.01); *G01N 2333/96466* (2013.01); *G01N 2500/10* (2013.01); *G01N 2500/04* (2013.01); *C12Q 1/37* (2013.01)
USPC ........................... 435/6.18; 435/6.13; 435/18

(58) Field of Classification Search
None
See application file for complete search history.

(56) References Cited

U.S. PATENT DOCUMENTS

| | | | |
|---|---|---|---|
| 6,974,667 B2 * | 12/2005 | Horne et al. | ................ 435/6.14 |
| 2009/0060962 A1 | 3/2009 | Castiel et al. | |
| 2011/0165607 A1 | 7/2011 | Takeda et al. | |

FOREIGN PATENT DOCUMENTS

WO    WO 2009/142268 A1    11/2009

OTHER PUBLICATIONS

Kezic et al. (J Invest Dermatol. Aug. 2008;128(8):2117-9. Epub Feb. 28, 2008).*
"Abstracts for the International Investigative Dermatology 2008," Journal of Dermatological Science, Apr. 1, 2008, 50(2):e1-e285, particularly e92, left column, paragraph 539, Takeda et al., "Neutral cysteine protease bleomycin hydrolase is essential for the formation of amino acids from deiminated filaggrin as natural moisturizing factor of the stratum corneum."
Broccardo et al., "Peeling off the layers: Skin taping and a novel proteomics approach to study atopic dermatitis," J. Allergy Clin. Immunol., Nov. 1, 2009, 124(5):1113-1115.e11.
"JSID Abstracts," Journal of Dermatological Science, Dec. 1, 2009, 56(3):e1-349, particularly e17, left column, paragraph 97, P0-01, Kamata et al., "Characterization of neutral cysteine protease bleomycin hydrolase in human epidermis."
Kamata et al., "Neutral Cysteine Protease Bleomycin Hydrolase is Essential for the Breakdown of Deiminated Filaggrin into Amino Acids," J. Biol. Chem., Mar. 13, 2009, 284(19):12829-12836.
Schwartz et al., "The neutral cysteine protease bleomycin hydrolase is essential for epidermal integrity and bleomycin resistance," Proc. Natl. Acad. Sci. USA, Apr. 1, 1999, 96:4680-4685.
International Search Report cited in related International Patent Application No. PCT/JP2010/071599, completed Jan. 17, 2011.
Kamata et al., "Regulatory mechanisms of a natural moisturizing factor-generating enzyme, bleomycin hydrolase—its relevance to atopic dermatitis," Journal of Investigative Dermatology, Apr. 2010, 130(Supp. 1):S73, Abstract 436.

* cited by examiner

*Primary Examiner* — Manjunath Rao
*Assistant Examiner* — Jae W Lee
(74) *Attorney, Agent, or Firm* — Foley & Lardner LLP

(57) ABSTRACT

The present invention provides a method for screening and evaluating ameliorants of dry skin caused by atopic dermatitis, comprising: evaluating a candidate drug as being an ameliorant of dry skin caused by atopic dermatitis in the case the candidate drug significantly increases expression and/or activity of bleomycin hydrolase in comparison with a control drug.

1 Claim, 22 Drawing Sheets

Specimen 1    Specimen 2

2  5  10  20    2  5  10  20

No. of tape strippings

Specimen  T  N  A  M

T, A: Dry skin not perceived
N: Somewhat dry, M: Dry

Fig.13
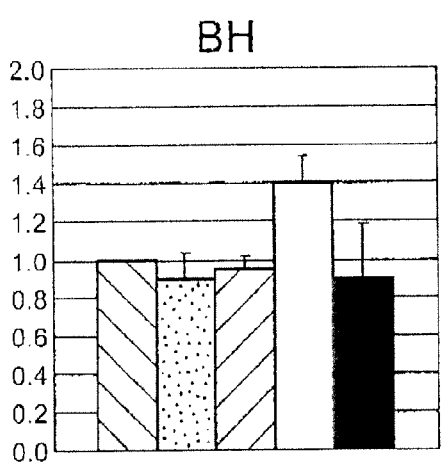
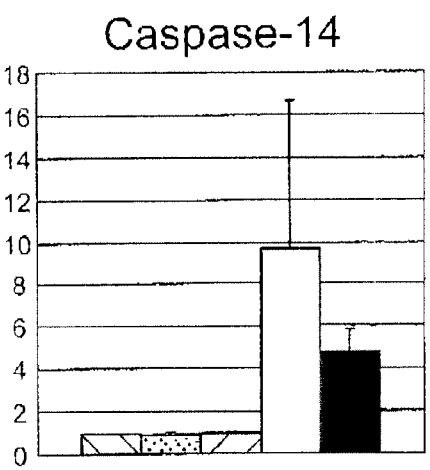
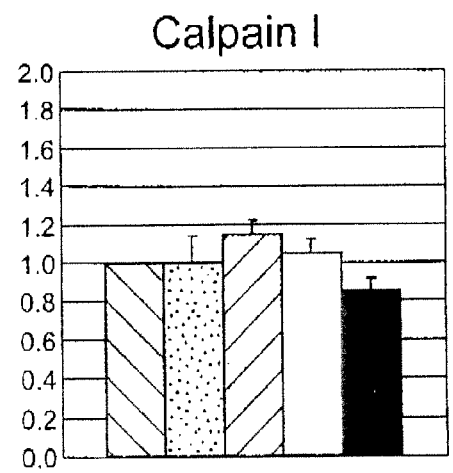

Fig.15

| Name | Sequence |
|---|---|
| BH-1216 KpnI (forward) | 5´-CCGGGTACCATCAGAGTTCCTTAGAA-3´ |
| BH-1016 KpnI (forward) | 5´-CCGGGTACCCAAGGTTTTTACAATCT-3´ |
| BH-816 KpnI (forward) | 5´-CACGGTACCTGGGTAGTGTTCTTGAA-3´ |
| BH-616 KpnI (forward) | 5´-CGAGGTACCTCCTTGTGACATATCGA-3´ |
| BH-444 KpnI (forward) | 5´-AATGGTACCTTGGAGCGGGCCTGA-3´ |
| BH-216 KpnI (forward) | 5´-AATGGTACCAGGGGGGAGTTTTGTCC-3´ |
| BH-171 KpnI (forward) | 5´-AATGAAGGTACCTCAGCCTCCCCGCCG-3´ |
| BH-134 KpnI (forward) | 5´-ACGGGTACCAGCCGGTTTCCTTTTTC-3´ |
| BH-105 KpnI (forward) | 5´-AATGGTACCTGCGAGAGACAGGTCG-3´ |
| BH+1 MluI (reverse) | 5´-TAAATACGCGTTGGCGCCCACGCTGCCG-3´ |

Fig.16

| Probe | Sequence |
|---|---|
| Sp-1 | (sense) 5'-TCTCCCAGCCTCAGTCTCCCAGCCTCAG-3'<br>(anti-sense) 5'-AGAGGGTCGGAGTCAGAGGGTCGGAGTC-3' |
| MZF-1 | (sense) 5'-CGCGAGGGGGGAGTTCGAGGGGGGAGTTT-3'<br>(anti-sense) 5'-GCGCTCCCCCCTCAAGCTCCCCCCTCAAA-3' |
| IRF-1/2 | (sense) 5'-CCGGTTTCCTTTTTCGCGGTTTCCTTTTTC-3'<br>(anti-sense) 5'-GGCCAAAGGAAAAAGCGCCAAAGGAAAAAG-3' |
| GATA-1 | (sense) 5'-GCAGCGCAATCCCGGCAGCGCAATCCCGGC-3'<br>(anti-sense) 5'-CGTCGCGTTAGGGCCGTCGCGTTAGGGCCG-3' |

Fig.17

| Gene | Sequence | Annealing |
|---|---|---|
| BH | (forward) 5'-TGTGGTTTGGCTGTGATGTT-3'<br>(reverse) 5'-GCACCATCCTGATCATCCTT-3' | 55°C |
| Calpain-I | (forward) 5'-ACATGGAGGCCATCACTTTC-3'<br>(reverse) 5'-GGTCCACGTTGTTCCACTCT-3' | 55°C |
| Sp-1 | (forward) 5'-AGCGACCAAGATCACTCCAT-3'<br>(reverse) 5'-TGGGTGACTCAATTCTGCTG-3' | 58°C |
| MZF-1 | (forward) 5'-TAGAGCCCTTGCTCACGTTT-3'<br>(reverse) 5'-GGGCATTGTCTAGGTGGAAA-3' | 58°C |
| IRF-1* | (forward) 5'-GAACTCCCTGCCAGATATCGAG-3'<br>(reverse) 5'-TGCTCTTAGCATCTCGGCTGGA-3' | 58°C |
| IRF-2* | (forward) 5'-TGGATGCATGCGGCTAGA-3'<br>(reverse) 5'-CATCTGAAATTCGCCTTCC-3' | 58°C |
| GATA-1 | (forward) 5'-ATTGTCAGTAAACGGGCAGG-3'<br>(reverse) 5'-TCTGAATACCATCCTTCCGC-3' | 58°C |

Fig. 18
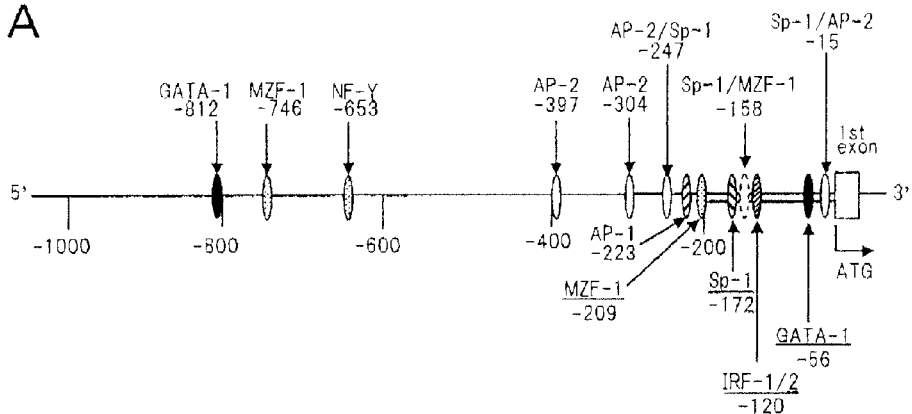
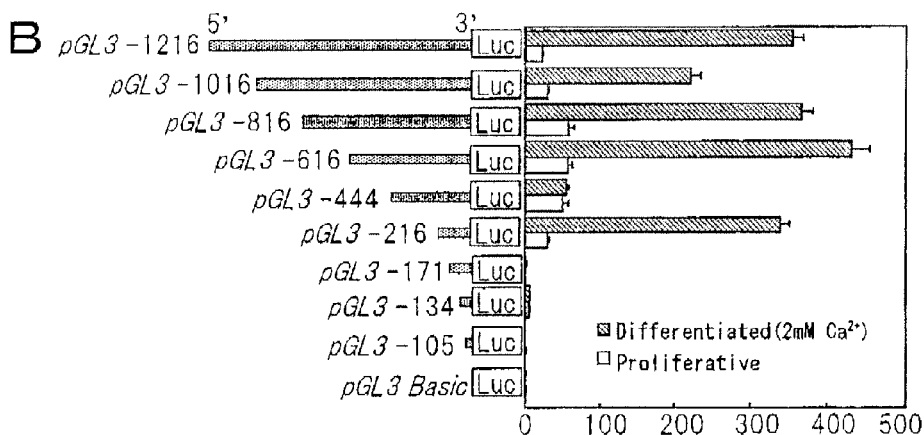
C -216                                                                                   -171
5'-AGGGGGGAGTTTTGTCCCTCCGCGGACCCCGTTTCTCCCAGCCTCAGCCT
   MZF-1                                    -134    Sp-1
CCCCGCCGCCGCCGCCGCCGCCGCCGCCGCCGAGCCGGTTTCCTTTTTCC
Sp-1/MZF-1                                    IRF-1/2
           -105
GGCGCTCCGGTGCGAGAGACAGGTCGGGCCCCCTAGGCAGCGAGCCGCAG
CGCAATCCCGGCGCTCGCCCAAGGACCCTGGAAGCTACCGTTACCCCGCC
GATA-1/2        +1                                   Sp-1/AP-2
GGCAGCGTGGGCGCCA-3'

Fig.20
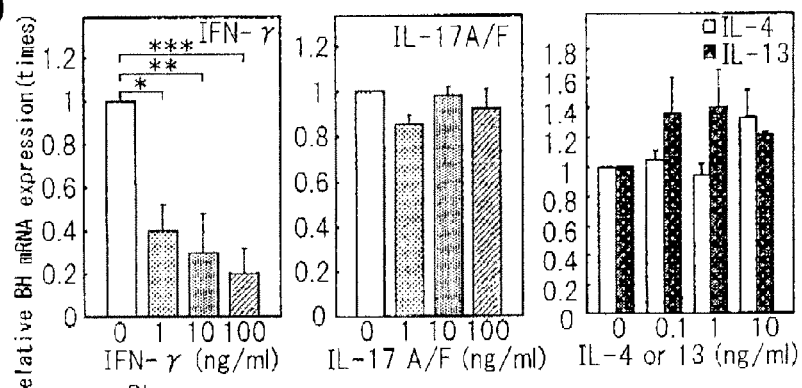
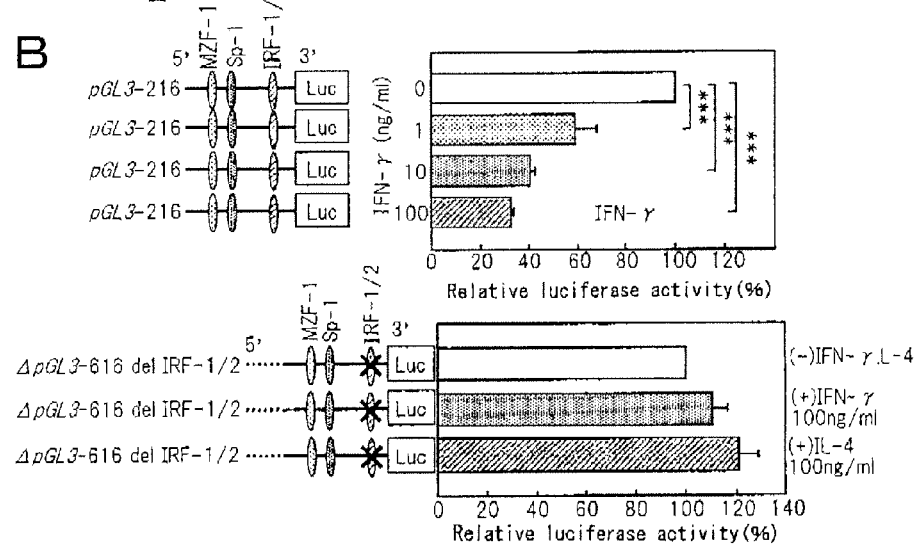
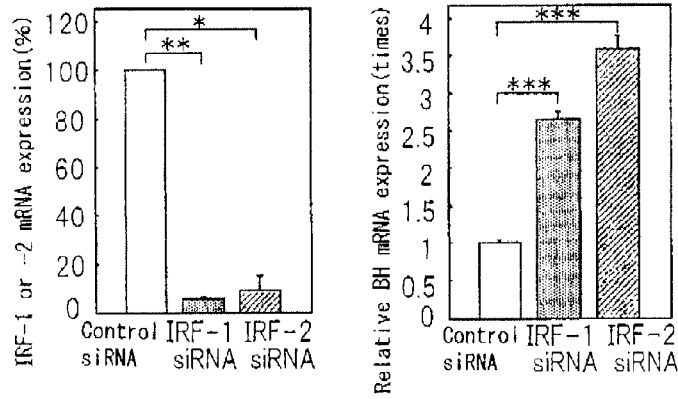

Fig.23
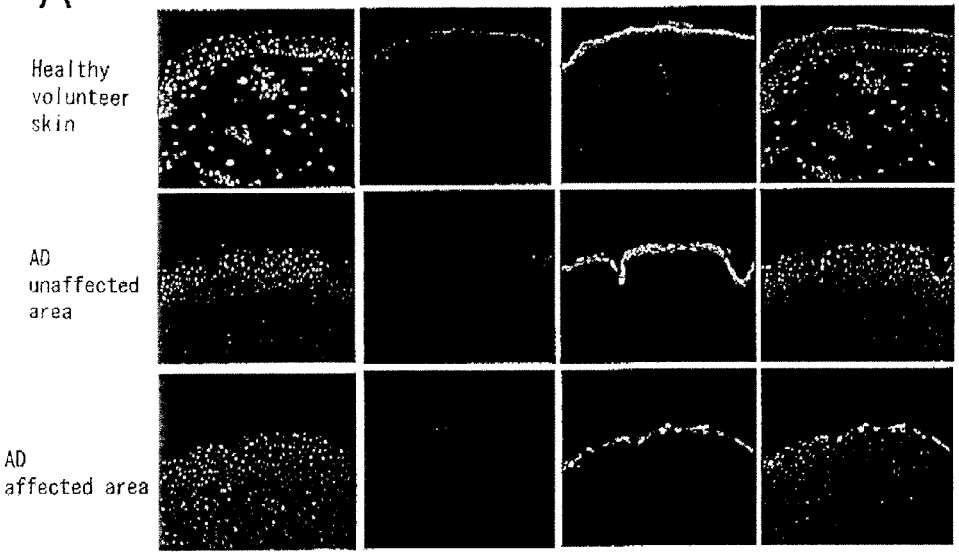
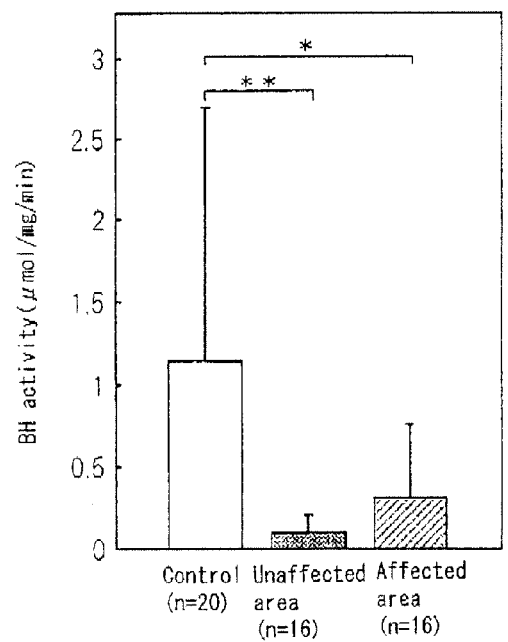

SEQUENCE LISTING

```
<160> NUMBER OF SEQ ID NOS: 41

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtggtttgg ctgtgatgtt                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcaccatcct gatcatcctt                                                  20

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 3
tcctcgagtc tgtatcagag cagctaca                                      28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgaacacgcg tccgagctgc tcatggcg                                      28

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgggtacca tcagagttcc ttagaa                                        26

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taaatacgcg ttggcgccca cgctgccg                                      28

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaccccgtt tcagcctccc cgcc                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggcggggagg ctgaaacggg gtcc                                          24

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 9
gactcagcaa cgcggttttg tccctccgc                                29

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcggagggac aaaaccgcgt tgctgagtca                               30

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccgccgagc ctccggcgct cc                                       22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggagcgccgg aggctcggcg gc                                       22

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgggtaccc aaggttttta caatct                                   26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacggtacct gggtagtgtt cttgaa                                   26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 15
cgaggtacct ccttgtgaca tatcga                                          26

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aatggtacct tggagcgggc ctga                                            24

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aatggtacca gggggagtt ttgtcc                                           26

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aatgaaggta cctcagcctc cccgccg                                         27

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgggtacca gccggtttcc tttttc                                          26

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aatggtacct gcgagagaca ggtcg                                           25

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 21
tctcccagcc tcagtctccc agcctcag                                          28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
agagggtcgg agtcagaggg tcggagtc                                          28

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cgcgaggggg gagttcgagg ggggagttt                                         29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gcgctccccc ctcaagctcc cccctcaaa                                         29

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ccggtttcct ttttcgcggt ttcctttttc                                        30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ggccaaagga aaaagcgcca aaggaaaaag                                        30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 27
gcagcgcaat cccggcagcg caatcccggc                                      30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
cgtcgcgtta gggccgtcgc gttagggccg                                      30

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acatggaggc catcactttc                                                 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtccacgtt gttccactct                                                 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agcgaccaag atcactccat                                                 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgggtgactc aattctgctg                                                 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tagagccctt gctcacgttt                                                    20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gggcattgtc taggtggaaa                                                    20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaactccctg ccagatatcg ag                                                 22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgctcttagc atctcggctg ga                                                 22

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tggatgcatg cggctaga                                                      18

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
catctgaaat tcgccttcc                                                     19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 39
attgtcagta aacgggcagg                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tctgaatacc atccttccgc                                              20

<210> SEQ ID NO 41
<211> LENGTH: 216
<212> TYPE: DNA
<213> ORGANISM: Homo sapiens

<400> SEQUENCE: 41 agggggagt tttgtccctc cgcggacccc gtttctccca gcctcagcct ccccgccgcc    60
gccgccgccg ccgccgccgc cgagccggtt tccttttcc ggcgctccgg tgcgagagac   120
aggtcgggcc ccctaggcag cgagccgcag cgcaatcccg gcgctcgccc aaggaccctg   180
gaagctaccg ttaccccgcc ggcagcgtgg gcgcca                            216
```

METHOD FOR SCREENING AMELIORANTS OF DRY SKIN CAUSED BY ATOPIC DERMATITIS USING BLEOMYCIN HYDROLASE ACTIVITY AS INDICATOR

CROSS-REFERENCE TO RELATED APPLICATIONS

This application is a National Stage application of PCT/JP2010/071599, filed Dec. 2, 2010, which claims priority from Japanese application JP 2009-275909, filed Dec. 3, 2009.

The instant application contains a Sequence Listing which has been submitted in ASCII format via EFS-WEB and is hereby incorporated by reference in its entirety. Said ASCII copy, created on Jun. 23, 2014, is named 053466-0530 SL.txt and is 9,844 bytes in size.

TECHNICAL FIELD

The present invention provides a method for screening and evaluating ameliorants of dry skin, and particularly dry skin caused by atopic dermatitis, a method for improving or preventing dry skin caused by atopic dermatitis, and a method for diagnosing dry skin caused by atopic dermatitis.

BACKGROUND ART

Keratin fibers present in the granular layer of the epidermis aggregate by binding to a protein referred to as filaggrin during keratinization and produce a characteristic morphology referred to as a "keratin pattern". Although a precursor substance of filaggrin known as profilaggrin (consisting of an arrangement of 10 to 12 filaggrin units) is present in large amounts in keratohyalin granules within granular cells, together with the formation of filaggrin monomers, keratin fibers are caused to aggregate by dephosphorylation during keratinization. Subsequently, the aggregated keratin fibers are subjected to deimination by the action of an enzyme known as peptidyl arginine deiminase (PAD), are released as keratin, and are subsequently decomposed to amino acids and the like in the upper layer of the horny layer. These amino acids are referred to as natural moisturizing factors (NMF), play an important role in maintaining the moisture content of the horny layer, and are known to possess the ability to absorb ultraviolet light (Blank, I. H., J.I. Dermatol., 18, 433 (1952); Blank, I. H., J.I. Dermatol., 21, 259 (1953)).

Ever since amino acids functioning as the main component of NMF were determined to originate in filaggrin, research has been conducted on the correlation between disease states presenting with dry skin and filaggrin. Amino acid levels in the horny layer have recently been determined to decrease in dry skin associated with conditions such as senile xerosis or atopic diseases (Horii, I. et al., Br. J. Dermatol., 121, 587-592 (1989); Tanaka, M. et al., Br. J. Dermatol., 139, 618-621 (1989)).

PAD deiminates filaggrin by acting on arginine residues, and converts them to citrulline residues. As a result of filaggrin being deiminated in this manner, the affinity between filaggrin and keratin fibers weakens and the keratin fibers are released, and as a result thereof, filaggrin becomes susceptible to the action of proteases, and this is ultimately thought to lead to its decomposition to NMF.

The inventor of the present invention identified calpain 1 as an enzyme that decomposes filaggrin deiminated by PAD, and determined that the decomposition products thereof in the form of small peptide fragments are decomposed to amino acid units, namely NMF, by bleomycin hydrolase (BH) (Journal of Investigative Dermatology (2008), Volume 128, Abstracts, 590, 539; Joint Conference of the 30th Annual Meeting of the Molecular Biology Society of Japan and 80th Annual Scientific Meeting of the Japanese Biochemical Society, Collection of Abstracts, p. 533; Journal of Biological Chemistry, 284, No. 19, pp. 12829-12836, 2009, 3P-0251; and, Japanese Patent Application No. 2008-135944 (to be referred to as JP944).

More recently, some atopic dermatitis is known to be caused by a genetic abnormality of the profilaggrin gene, and this genetic abnormality is observed in roughly 5% to 50% of atopic dermatitis patients (Smith, F. J. D., et al., Nat. Genet. 38: 337-342 (2006): Aileen Sandilands, at al., J.I. Dermatol., 127, 1282-1284 (2007); and, Nomura, T. et al., J.I. Dermatol., 128(6): 1436-41 (2008)). However, the skin of atopic dermatitis patients is not necessarily associated with a dramatic decrease in expression of filaggrin.

PRIOR ART DOCUMENTS

Non-Patent Documents

Non-Patent Document 1: Blank, I. H., J.I. Dermatol., 18, 433 (1952)
Non-Patent Document 2: Blank, I. H., J.I. Dermatol., 21, 259 (1953)
Non-Patent Document 3: Horii, I. et al., Br. J. Dermatol., 121, 587-592 (1989)
Non-Patent Document 4: Tanaka, M. et al., Br. J. Dermatol., 139, 618-621 (1989)
Non-Patent Document 5: Kamata, et al., J. Biochem., 141, 69-76 (2007)
Non-Patent Document 6: Journal of Investigative Dermatology (2008), Volume 128, Abstracts, S90, 539
Non-Patent Document 7: Joint Conference of the 30th Annual Meeting of the Molecular Biology Society of Japan and 80th Annual Scientific Meeting of the Japanese Biochemical Society, Collection of Abstracts, p. 583, 3P-0251
Non-Patent Document 8: Journal of Biological Chemistry, 284; No. 19, pp. 12829-12836, 2009
Non-Patent Document 9: Smith, F. J. D. et al., Nat. Genet. 38: 337-42 (2006)
Non-Patent Document 10: Aileen Sandilands, et al., J.I. Dermatol., 127, 1282-1284

SUMMARY OF THE INVENTION

Problems to be Solved by the Invention

An object of the present invention is to provide a method for screening drugs that improve or prevent dry skin caused by atopic dermatitis based on a novel mechanism of the occurrence of rough skin attributable to fluctuations in expression of an NMF-producing enzyme, a method for evaluating dry skin caused by atopic dermatitis, a method for improving or preventing dry skin caused by atopic dermatitis, and a method for diagnosing dry skin caused by atopic dermatitis.

Means for Solving the Problems

In the aforementioned JP944, the inventors of the present invention determined that increased activity of bleomycin hydrolase improves the barrier function of skin through the production of NMF. In this manner, bleomycin hydrolase is thought to be act in the final stage of NMF production. However, it is interesting to note with respect to dry skin occurring due to atopic dermatitis that, since expression of filaggrin continues to be observed in numerous atopic dermatitis patients, this phenomenon is predicted to be caused by that other than an abnormality of the filaggrin gene.

Based on the hypothesis that decreased expression of bleomycin hydrolase in human skin is not only related to a decrease in the skin's barrier function due to abnormality in the mechanism by which NMF is produced, but also to atopic dermatitis primarily caused by an immune disorder or dry skin and the like caused by atopic dermatitis, the inventors of the present invention verified fluctuations in the expression of this enzyme by conducting tests on dry skin in humans and analyzed the mechanism by which its expression is controlled. As a result, the inventors of the present invention found that decreased expression of bleomycin hydrolase is related to dry skin caused by atopic dermatitis, and that a control region that clearly induces expression of the enzyme is present in the 5' flanking region of a gene that encodes that enzyme. More specifically, the inventors of the present invention cloned the 5' flanking region of BH. A region important for BH promoter activity was identified −216 bp upstream in a deletion analysis thereof. An electrophoretic mobility shift assay clearly demonstrated that MZF-1, Sp-1 and interferon regulatory factor (IRF)-1/2 are able to bind to this region in vitro. Moreover, BH promoter activity decreased considerably when a site-specific mutation was induced in the MZF-1 and Sp-1 motifs. These data suggested that BH expression is up-regulated through MZF-1 and Sp-1. It is interesting to note that that the Th1 cytokine, interferon (IFN)-γ significantly decreased expression of BH. The inhibitory effect of IFN-γ on BH expression was demonstrated in an analysis using site-specific mutagenesis and small interfering RNA. Although the Th2 cytokine, IL-4, did not demonstrate any direct action whatsoever on BH expression, it down-regulated MZF-1 and Sp-1 in cultured keratinocytes. Thus, this suggested that IL-4 is able to act as a suppressor of BH regulation. Finally, the expression of BH was investigated in the skin of patients suffering from AD. Since BH activity and expression decreased considerably in skin affected by AD, a defect was suggested to be present in the filaggrin decomposition pathway in AD. As has been described above, the inventors of the present invention found that transcription of BH is likely regulated both during differentiation and inflammation, thereby leading to completion of the present invention.

Thus, the present application includes the inventions indicated below.

(1) A method for screening and evaluating ameliorants of dry skin caused by atopic dermatitis, comprising evaluating a candidate drug as being an ameliorant of dry skin caused by atopic dermatitis in the case the candidate drug significantly increases expression and/or activity of bleomycin hydrolase in comparison with a control drug.

(2) The method of (1), wherein expression and/or activity of bleomycin hydrolase is judged to have increased significantly in the case the transcription activity of a gene that encodes bleomycin hydrolase has increased significantly in comparison with that of a control.

(3) The method of (2), wherein the transcription activity is judged to have increased significantly in the case binding activity of transcription factors IRF-1, IRF-2, MZF-1, Sp-1 and/or GATA-1 to the transcription regulatory region of a gene that encodes bleomycin hydrolase has increased significantly in comparison with that of a control.

(4) A method for improving or preventing dry skin caused by atopic dermatitis by significantly increasing expression and/or activity of bleomycin hydrolase in skin tissue.

(5) The method of (4), wherein the expression and/or activity is significantly increased by increasing the transcription activity of a gene that encodes bleomycin hydrolase.

(6) The method of (5), wherein the expression and/or activity is significantly increased by increasing binding activity of transcription factors IRF-1, IRF-2, MZF-1, Sp-1 and/or GATA-1 to the transcription regulatory region of a gene that encodes bleomycin hydrolase.

(7) A method for diagnosing predisposition to dry skin caused by atopic dermatitis, comprising diagnosing a tendency towards dry skin caused by atopic dermatitis in the case expression and/or activity of bleomycin hydrolase in skin tissue is significantly decreased in comparison with that of control skin, while diagnosing the absence of a tendency towards dry skin caused by atopic dermatitis if it is equal to or greater than that of the control skin.

(8) The method of (7), wherein the expression and/or activity is judged to be significantly decreased in the case the transcription activity of a gene that encodes bleomycin hydrolase is significantly decreased in comparison with that of a control.

(9) The method of (8), wherein the transcription activity is judged to be decreased in the case binding activity of transcription factors IRF-1, IRF-2, MZF-1, Sp-1 and/or GATA-1 is significantly decreased in comparison with that of a control.

Effects of the Invention

Novel ameliorants of dry skin caused by atopic dermatitis can be found based on the novel mechanism of the occurrence of dry skin established by the present invention attributable to fluctuations in the expression of bleomycin hydrolase, and particularly on a screening system that uses expression and/or activity of bleomycin hydrolase as an indicator. Moreover, the method of the invention of the present application is also considered to be applicable to searching for ameliorants of ordinary dry skin not caused by atopic dermatitis. In fact, as described in examples of the present application, in a group demonstrating low levels of expression and/or activity of bleomycin hydrolase, the barrier function of the skin (transepidermal water loss: TEWL) decreased significantly along with a decrease in horny layer moisture content.

BRIEF DESCRIPTION OF THE DRAWINGS

FIG. 13 shows graphs indicating the relationship between expression of transcription factors SP1, MZF-1 and GATA-1 and UV irradiation.

FIG. 15 shows primers (SEQ ID NOS 5, 13-20 and 6, respectively, in order of appearance) used to prepare continuous 5'-deletion mutants of a 5' flanking region of BH by PCR.

FIG. 16 shows primers (SEQ ID NOS 21-28, respectively, in order of appearance) used to analyze transcription levels of BH and related factors by quantitative real-time RT-PCR.

FIG. 17 shows probes (SEQ ID NOS 1-2 and 29-40, respectively, in order of appearance) used to analyze electrophoretic mobility shift FIG. 18A shows a schematic diagram of a 5' flanking region of human BH. Putative transcription factor binding sites within the 5' flanking region were determined by a search using the Genome Net MOTIF program. FIG. 18B shows BH promoter regions as determined by deletion analysis. In FIG. 18C, putative transcription factor binding sites indicating the nucleotide sequence of a region from −216 to −1 that includes the minimum BH promoter sequence and the putative transcription binding sites (SEQ ID NO: 41).

FIG. 20A shows the results of real-time RT-PCR analyses of BH expression. The graphs indicate the effects of cytokines Th1, Th2 and Th17 on BH gene expression. FIG. 20B shows the results of mutation analyses of IRF-1/2 binding sites. The graphs indicate BH promoter activity in cultured keratinocytes in the presence of IFN-γ. Keratinocytes were transfected with pGL3-216 containing intact IRF-1/2 binding sites of BH promoter regions followed by treating for 24 hours with IFN-γ (upper panel). Keratinocytes were transfected with ΔpGL3-616 (IRF-1/2 deletion mutants) followed by treating for 24 hours in the presence or absence of IFN-γ or IL-4 at 10 ng/ml (lower panel). FIG. 20(C) shows the results of measuring IRF-1 and IRF-2 gene expression levels using small interfering RNA (siRNA) to judge whether or not IRF-1/2 are essential mediators of IFN-γ-induced down-regulation of BH. Keratinocytes were transfected with siRNA (40 nM) of IRF-1 or IRF-2 followed by culturing for 24 hours, treating with IFN-γ at 10 ng/ml and isolating RNA after further culturing for 24 hours. The panel on the right indicates the silencing effects of IRF-1 and IRF-2.

FIG. 23A indicates the simultaneous localization of BH and filaggrin in the granular layer as demonstrated by double staining with anti-BH antibody and anti-filaggrin antibody in normal epidermis FIG. 23B indicates the BH activities of extracts obtained from affected skin and unaffected skin of an AD patient.

DESCRIPTION OF THE PREFERRED EMBODIMENTS

In a first aspect thereof, the present invention provides a method for screening and evaluating ameliorants of dry skin caused by atopic dermatitis, comprising evaluating a candidate drug as being an ameliorant of dry skin caused by atopic dermatitis in the case the candidate drug significantly increases expression and/or activity of bleomycin hydrolase in comparison with a control drug.

Bleomycin hydrolase is a cytoplasmic cysteine peptidase having a molecular weight of 250 kDa to 280 kDa (hexamer), and was initially known to have the function of metabolic deactivation of the glycopeptide bleomycin frequently used in cancer combination chemotherapy. Bleomycin hydrolase contains an active site residue characteristic of the papain superfamily of cysteine proteases, and its encoding gene is present at gene locus 17q11.2 in humans (Takeda, et al., J. Biochem., 119, 29-36, 1996). It is present in all tissues, and although it is also known to be present in skin (Kamata, et al., J. Biochem., 141, 69-76, 2007), its relationship with filaggrin was completely unknown prior to the determination thereof by the inventor of the present invention.

Figure 8:
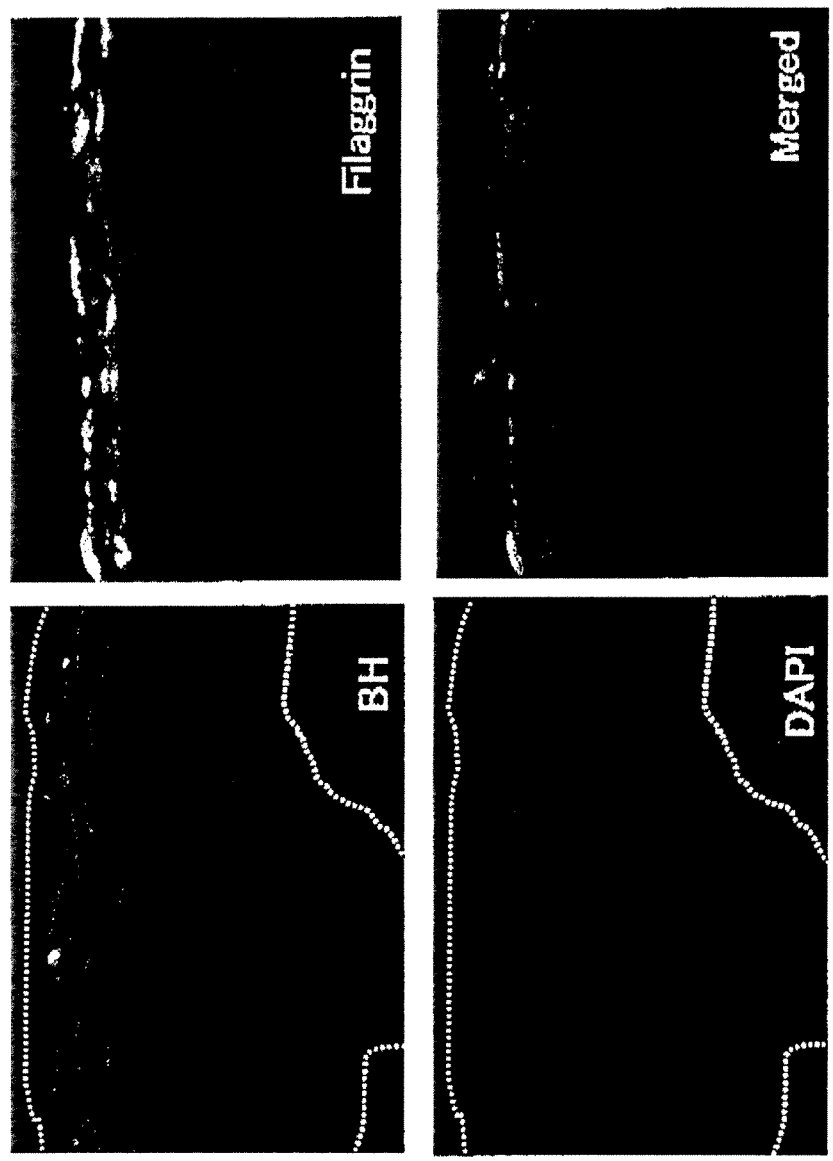
FIG. 8 shows tissue staining images indicating the localization of bleomycin hydrolase and filaggrin in normal skin.
Figure 9:
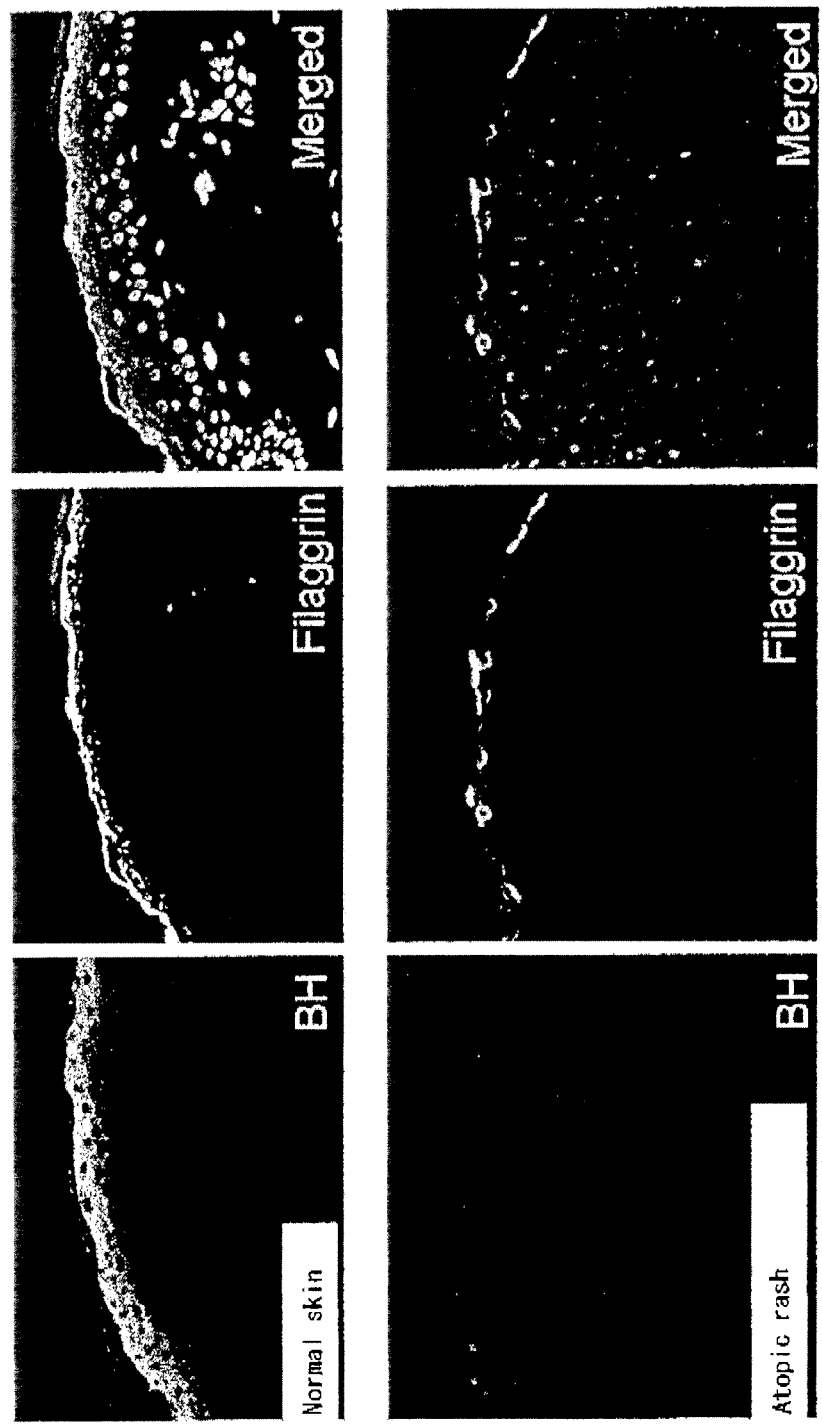
FIG. 9 shows tissue staining images indicating the localization of bleomycin hydrolase and filaggrin in the skin of a patient with atopic dermatitis.

Based on the results of tissue staining, bleomycin hydrolase was determined to be expressed in large amounts in the upper layer of the epidermis in normal skin in the same manner as filaggrin (FIG. 8). On the other hand, expression of bleomycin hydrolase and filaggrin decreases at the sites of atopic rashes in atopic dermatitis patients (FIG. 9). This strongly suggests that an abnormality in this enzyme system, and not an abnormality of the profilaggrin gene, is the cause of atopic dermatitis. In addition, bleomycin hydrolase activity is significantly lower in not only affected areas, but also unaffected areas, in the skin of atopic dermatitis patients (data not shown).

Figure 10:
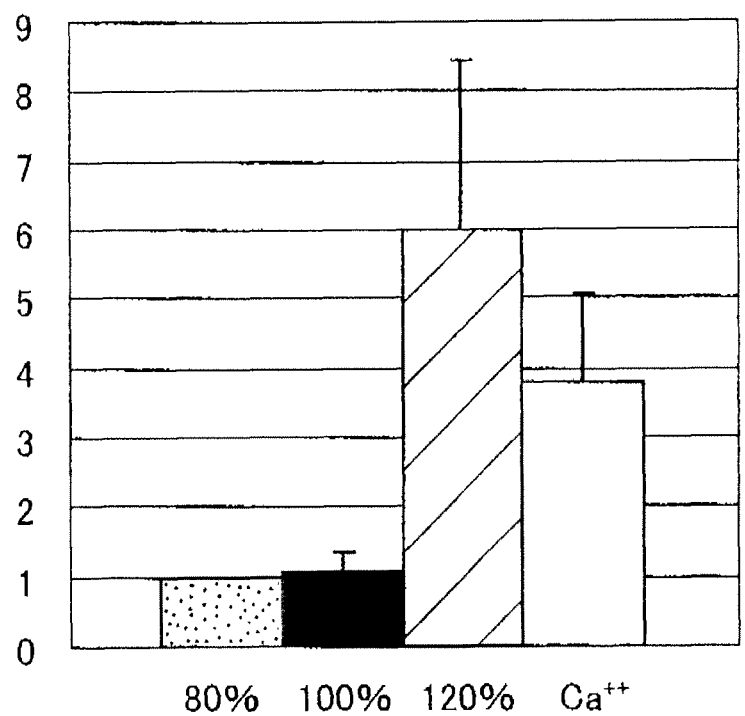
FIG. 10 is a graph indicating the relationship between the differentiation of keratinocytes and expression level of bleomycin hydrolase as determined using quantitative PCR. Values on the vertical axis represent relative amounts based on a value of 1 for the expression level at 80% confluence.

Moreover, as a result of studying fluctuations in expression levels of bleomycin hydrolase using cultured keratinocytes, in contrast to this enzyme not being expressed at a high level in undifferentiated keratinocytes, it was found to be highly expressed in differentiated keratinocytes that had reached confluence, hardly expressed at all in basal cells, and highly expressed in cells in which differentiation had progressed and had transformed into epidermal cells (FIG. 10). This result supports the result obtained from cell staining as previously described.

Measurement of the expression and/or activity of bleomycin hydrolase according to the present invention can be carried out quantitatively or qualitatively in accordance with any arbitrary method able to be used to measured the expression and/or activity of this enzyme, such as an immunoassay method that utilizes antibody specific to bleomycin hydrolase, examples of which include ELISA using an enzyme label, RIA using a radioactive label, immunonephelometry, western blotting, latex agglutination and hemagglutination. Examples of types of immunoassays include competitive assays and sandwich assays. More specifically, measurement of the aforementioned activity can be carried out by, for example, utilizing the property of citrulline of being a substrate nearly specific to bleomycin hydrolase, and evaluating the decomposition of its fluorogenic substrate, Cit-MCA, with a fluorescence spectrophotometer. Measurement of the amount of bleomycin hydrolase can also be carried out by measuring the expression level of a gene that encodes the enzyme. In this case, the expression level of bleomycin hydrolase is preferably determined by measuring the amount of mRNA that encodes bleomycin hydrolase within cells. Extraction of mRNA and quantitative or qualitative measurement of the amount thereof are known in the art, and can be carried out by various known methods, such as PCR, 3SR, NASBA or TMA. In addition, bleomycin hydrolase can also be qualitatively determined by in situ hybridization or through measurement of the biological activity thereof.

In the method for screening and evaluating ameliorants of dry skin caused by atopic dermatitis of the present invention, a candidate drug is evaluated as being an ameliorant of dry skin caused by atopic dermatitis in the case the candidate drug significantly increases the expression and/or activity of bleomycin hydrolase in comparison with a control drug. Drugs screened in accordance with the method of the present invention are considered to be effective for dry skin, and particularly for dry skin caused by atopic dermatitis.

According to guidelines for the examination and treatment of atopic dermatitis of the Japan Dermatological Association, "atopic dermatitis" is defined as a disease associated with the primary complaint of itchy eczema that undergoes repeated exacerbation and improvement, and can be diagnosed based on the presence or absence of itching, and in terms of the characteristic rash thereof, the presence of acute lesions such as erythema, weeping erythema, papules, serous papules, scales or scabs, as well as chronic lesions such as infiltrative erythema, lichenified lesions, prurigo, scales or scabs. When used in the present description, "dry skin caused by atopic dermatitis" refers to dry skin associated with atopic dermatitis that has been definitively diagnosed according to the aforementioned definition, including genetic abnormalities of the filaggrin gene.

Examples of the screening method of the present invention include a method consisting of measuring an increase in the expression of mRNA that encodes bleomycin hydrolase in the presence of a drug to be tested, and a method consisting of inserting a promoter sequence involved in expression of bleomycin hydrolase into a luciferase gene vector, and directly measuring the degree of expression in the form of a promoter assay system. In the case of the latter, a region from −216 bp to −816 bp at which BH expression reaches a maximum is preferably used for the BH promoter region. In addition, a fluorescent protein such as Azami-Green commonly used in the art can be used to measure expression level instead of luciferase. The action of a drug on BH expression can be measured by introducing a vector containing a fused gene thereof into cells, culturing the cells in the presence of a drug, lysing the cells normally after 24 hours and measuring luciferase activity. Although commercially available normal human epidermal keratinocytes (NHEK, such as those available from Kurabo Industries, Ltd.) or immortalized HaCaT cells and the like can be used for the cells used for measurement, the cells used are not limited thereto. Measurement of luciferase activity is preferably carried out by using a luciferase assay kit such as that available from Roche Diagnostics K.K.

When used, in the present description, "significantly increases expression and/or activity of bleomycin hydrolase in comparison with a control drug" refers to the case in which the measured expression level, activity or both of bleomycin hydrolase is 120% or more, 150% or more, or 200% or more, respectively, in comparison with a drug that does not have an ameliorative effect on dry skin, and, particularly an ameliorative effect on dry skin caused, by atopic dermatitis.

Figure 11:
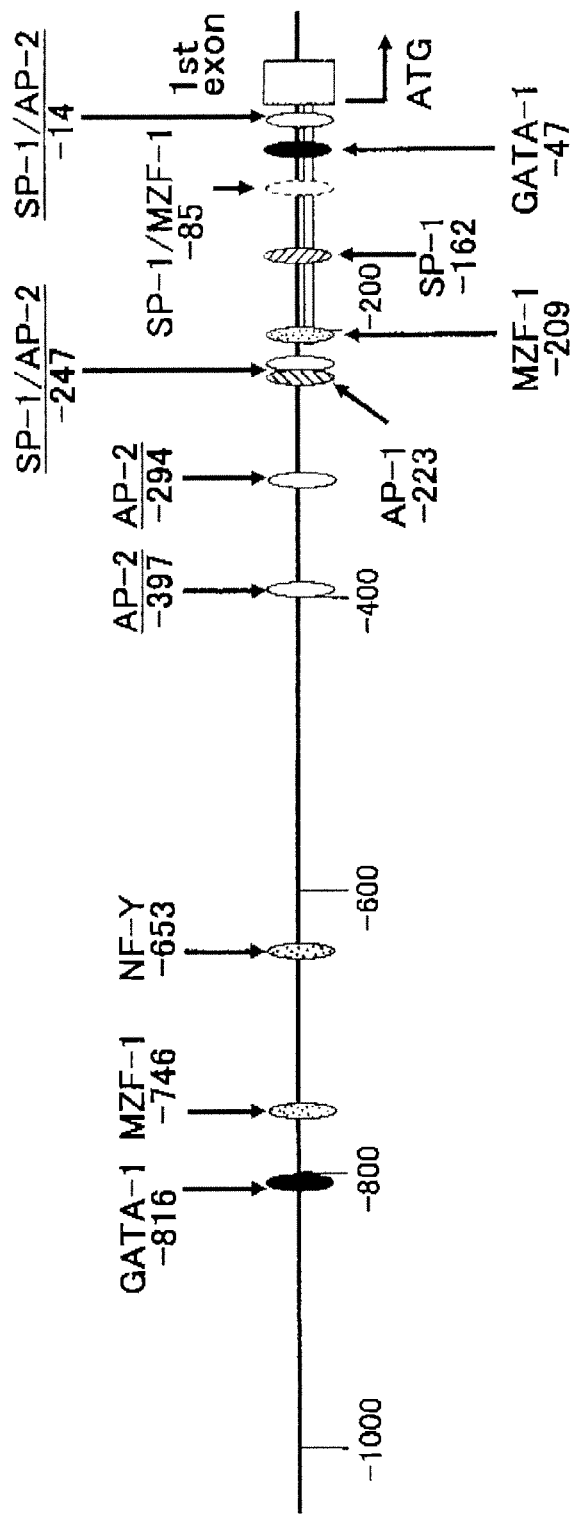
FIG. 11 is a schematic diagram showing a 5' flanking region of a gene that encodes bleomycin hydrolase.

Increasing the expression and/or activity of bleomycin hydrolase can also be achieved by increasing the transcription activity of a gene that encodes the enzyme. A 5' flanking region of a gene that encodes bleomycin hydrolase, and particularly a transcription regulatory region, and transcription factors that bind to that region, are shown in FIG. 11. The aforementioned transcription regulatory region has a region extending −216 bp to 1216 bp downstream from the sequence that encodes the enzyme. The transcription regulatory region preferably contains a region extending −816 bp downstream from the viewpoint of obtaining a high level of bleomycin hydrolase activity.

A region extending at least −216 bp downstream from the sequence encoding bleomycin hydrolase is to be contained in order to express this enzyme. Among the transcription factors described in FIG. 11, expression of bleomycin hydrolase is thought to be particularly enhanced by increasing the binding activities of IRF-1, IRF-2, MZF-1, Sp-1 and GATA-1 contained in this region. In fact, when expression of bleomycin hydrolase is increased by irradiating with ultraviolet (UV) light (data not shown), a correlation is observed between expression levels of MZF-1 and GATA-1 and UV intensity and irradiation time (FIG. 13).

Here, in the case the transcription activity of a gene encoding bleomycin hydrolase, or the binding activity of a transcription factor to the transcription regulatory region of that gene, is significantly increased by a candidate drug, such as by 120% or more, 150% or more or 200% or more, respectively, in comparison with a control drug, the expression level and/or activity of bleomycin hydrolase can be considered to be significantly increased.

Expression and/or activity of bleomycin hydrolase are also affected by cytokines. For example, interleukin-4 (IL-4), which is known to be involved in atopic dermatitis and is a type of Th2 cytokine, down-regulates expression of bleomycin hydrolase. This coincides with the low expression level of bleomycin hydrolase observed in the skin of atopic dermatitis patients. On the other hand, interferon-γ, which is a typical Th1 cytokine that has the opposite action of IL-4 of inhibiting production of IgE, significantly increases expression of bleomycin hydrolase. In addition, tumor necrosis factor-alpha (TNF-α), which is a Th2 cytokine representative of inflammatory cytokines, also significantly increases expression of this enzyme. In addition to these substances, expression and/or activity of bleomycin hydrolase is also increased by UV irradiation. Although the results thereof are not shown, the activity of bleomycin hydrolase in the skin of the cheeks or other location on the body susceptible to ultraviolet irradiation has been confirmed to be increased by UV irradiation.

In a second aspect thereof, the present invention provides a method for improving or preventing dry skin caused by atopic dermatitis by significantly increasing expression and/or activity of bleomycin hydrolase in skin tissue.

In the method for improving or preventing dry skin caused by atopic dermatitis of the present invention, the expression and/or activity of bleomycin hydrolase in the skin is significantly increased in comparison with, for example, the expression and/or activity in skin prior to undergoing this treatment method. "Significantly increased" refers to the case in which, for example, the expression and/or activity of bleomycin hydrolase is made to be a value of 120% or more, 150% or more or 200% or more.

In the method of the present invention, an arbitrary drug is used that significantly increases the expression and/or activity of bleomycin hydrolase. In addition, there are no limitations on the drug provided it increases the expression and/or activity of this enzyme. The drug and the like used in the method of the present invention can be applied to the skin in an arbitrary form provided it can be applied to skin and it is able to achieve the object of the present invention, and the drug may be applied alone or may be applied by incorporating with other arbitrary components. In addition, there are no limitations an the location of the skin where the drug is applied, and includes any skin on the body surface, including the scalp.

In a third aspect thereof, the present invention provides a method for diagnosing predisposition to dry skin caused by atopic dermatitis, comprising diagnosing a tendency towards dry skin caused by atopic dermatitis in the case expression and/or activity of bleomycin hydrolase in skin tissue is significantly decreased in comparison with that of control skin, while diagnosing the absence of a tendency towards dry skin caused by atopic dermatitis if it is equal to or greater than that of the control skin.

Whether or not the skin of a subject is dry can be judged based on the subjectivity of the subject or physician and the like, or can be judged objectively by measuring the moisture content of skin using a skin surface moisture analyzer. For example, as explained in Experiment 3 of the present description, whether or not a subject has dry skin can also be judged according to the subjectivity of a subject based on oiliness, susceptibility to drying and the like in accordance with the flow chart described in FIG. 6.

Although dry skin can be easily assessed, judging whether the skin of a subject is predisposed to dry skin caused by atopic dermatitis may be difficult. According to the diagnostic method of the present invention, a diagnosis can be made not only of the current status of a subject's skin, but also as to whether or not the subject is susceptible to dry skin caused by atopic dermatitis.

"Expression and/or activity of bleomycin hydrolase in skin tissue is significantly decreased in comparison with that of control skin" refers to the case in which measured expression and/or activity of bleomycin hydrolase is 80% or less, 70% or less, 60% or less, 50% or less, 30% or less or 10% or less in comparison with, for example, normal "control skin" judged to be moist skin by a physician from a dermatological perspective. "Equal to or greater than that of the control skin" refers to the case in which measured expression and/or activity of bleomycin hydrolase is, for example, 80% or more, 90% or more or 100% or more in comparison with, for example, normal "control skin" judged to be moist skin by a physician from a dermatological perspective.

Although collection of a skin horny layer sample to serve as a specimen can be carried out by an arbitrary method, tape stripping is preferable from the viewpoint of convenience. Tape stripping refers to a method by which a horny layer sample is collected by affixing a piece of pressure-sensitive adhesive tape to the skin surface layer and peeling off the tape so that the skin horny layer adheres to the peeled pressure-sensitive adhesive tape. Use of the tape stripping method makes it possible to measure expression and activity of bleomycin hydrolase simply by sampling the horny layer with a single piece of tape, thereby enabling non-invasive evaluation of dry skin caused by atopic dermatitis using bleomycin hydrolase as an indicator. In a preferable method employing tape stripping, the surface layer of the skin is first cleaned with ethanol, for example, to remove sebaceous matter, dirt and the like, a piece of pressure-sensitive adhesive tape cut to a suitable size (such as 5 cm×5 cm) is gently placed on the skin surface, the entire piece of tape is pressed flat onto the skin surface by applying uniform pressure, and the pressure-sensitive adhesive tape is subsequently peeled off while applying uniform force. The pressure-sensitive adhesive tape may be commercially available cellophane tape, and examples of pressure-sensitive adhesive tape that can be used include Scotch Super Strength Mailing Tape (3M) and Cellophane Tape (CelloTape®, Nichiban).

The following provides a more detailed explanation of the present invention by listing specific examples thereof. Furthermore, the present invention is not limited by these specific examples.

EXAMPLES

The following materials were used in the experiments.

Calpain I was purchased from EMD Biosciences Inc. Bleomycin hydrolase was prepared from human epidermal horny layer in accordance with Non-Patent Document 5. Human IL-4 and IFN-γ were purchased from Peprotech EC (London, England). Human IL-13 and IL-17A/F were produced by R&D Systems Inc. (Minneapolis, Minn.). Citrulline-4-methylcoumaryl-7-amide (Cit-MCA) was acquired from Bachem Bioscience Inc. (Bubendorf, Switzerland). Reagent grade products were used for all other chemical substances used.

Culturing of Keratinocytes

Normal human epidermal keratinocytes derived from neonatal epidermis (Kurabo, Osaka, Japan) were cultured in EpiLife medium (Cascade Biologics, Portland, Oreg.) containing low-concentration (0.03 mM) calcium and HKGS Growth Supplement (Cascade Biologics). All cells were incubated at 37° C. while supplying 5% $CO_2$ and were used within 4 passages. Cells were collected at 70% confluence, 100% confluence, 2 days after confluence and 2 days after confluence in 2 mM calcium.

Experiment 1

Bleomycin hydrolase is thought to act at the final stage of NMF production. In this case, there is the possibility of the expression of this enzyme decreasing in dry skin. In this experiment, a study was made as to whether or not a decrease in the expression and/or activity of bleomycin hydrolase in skin is related to dry skin.

Epidermal horny layer samples were collected by tape stripping consisting of affixing transparent pressure-sensitive adhesive tape (CelloTape®, Nichiban) to a skin surface on the arm followed by peeling off the tape. The tape adhered with the epidermal horny layer was cut into pieces, immersed in an extraction buffer (0.1 M Tris-HCl (pH 8.0), 0.14 M NaCl, 0.1% Tween-20, 1 ml), and subjected to ultrasonic treatment to prepare a horny layer extract. The horny layer extract was then subjected to western blotting. The anti-bleomycin hydrolase (BH) antibody used was prepared in accordance with the method of Kamata, et al. (Journal of Biological Chemistry, 2009). More specifically, the horny layer extract was subjected to SDS electrophoresis followed by transferring to Immobilon-P (Millipore), and after washing the transferred film, was allowed to react for 1 hour at room temperature with the anti-BH antibody. After removing the antibody by additional washing, the film was allowed to react with HRP-bound secondary antibody. After washing, the BH protein bands that were made to be luminescent with the ECL Plus Western Blotting Detection Kit (GE Healthcare) were printed onto an X-ray film, and expression levels were estimated based on the intensity thereof. The results are shown in FIGS. 1 and 2.

Figure 1:
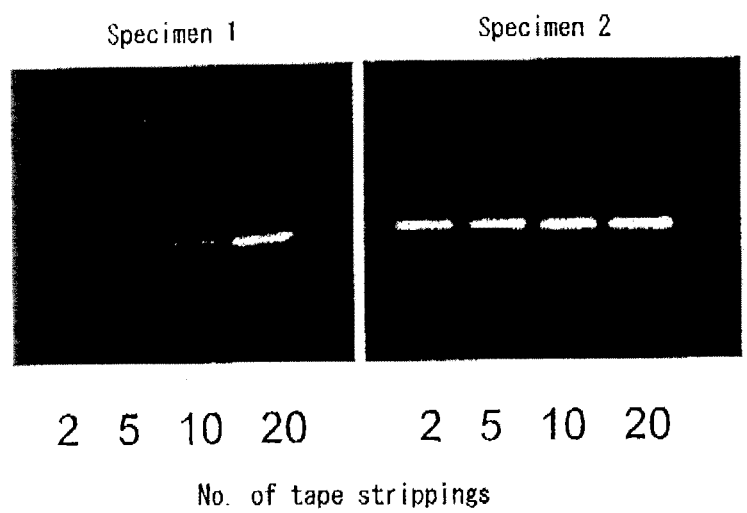
FIG. 1 shows Western blots indicating the relationship between the amount of bleomycin hydrolase and the number of tape strippings in human skin extracts obtained by tape stripping.
Figure 2:
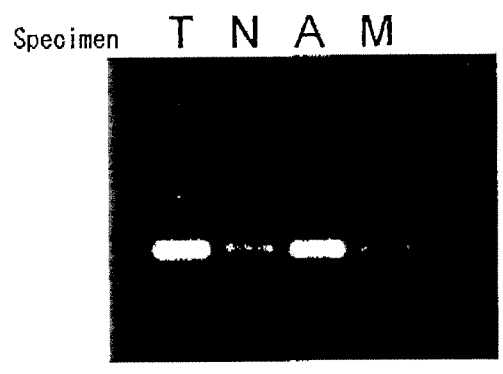
FIG. 2 shows a western blot indicating the relationship between the amount of bleomycin hydrolase and dry skin in human skin extracts. T and A represent samples obtained from subjects not sensing dryness, N represents a sample obtained from a subject sensing some degree of dryness, and M represents a sample obtained from a subject sensing dryness.

In FIG. 1, specimen 1 is a skin horny layer sample of a subject who was thought to have dry skin at the subject's own discretion, while specimen 2 is a skin horny layer sample of a healthy student not thought to have dry skin. In addition, specimens T and A in FIG. 2 are from subjects who did not perceive to have dry skin, specimen N was from a subject who perceived to have somewhat dry skin, and specimen M was from a subject who perceived to have dry skin. The expression level of bleomycin hydrolase in specimen 1 is low, while the expression level thereof in specimen 2 is high. On the basis thereof, specimens 1 and 2 can be determined to have been derived from dry skin and moist skin, respectively. In addition, based on the results using specimen 1, in dry skin the amount of bleomycin hydrolase can be determined to decrease more the closer to the skin surface serving as the production site of NMF. In the western blot of FIG. 2, specimens T and A indicate extracts obtained from subjects that did not particularly perceive dry skin, while specimens N and M are extracts from subjects who were strongly aware of having dry skin.

Experiment 2

Figure 3:
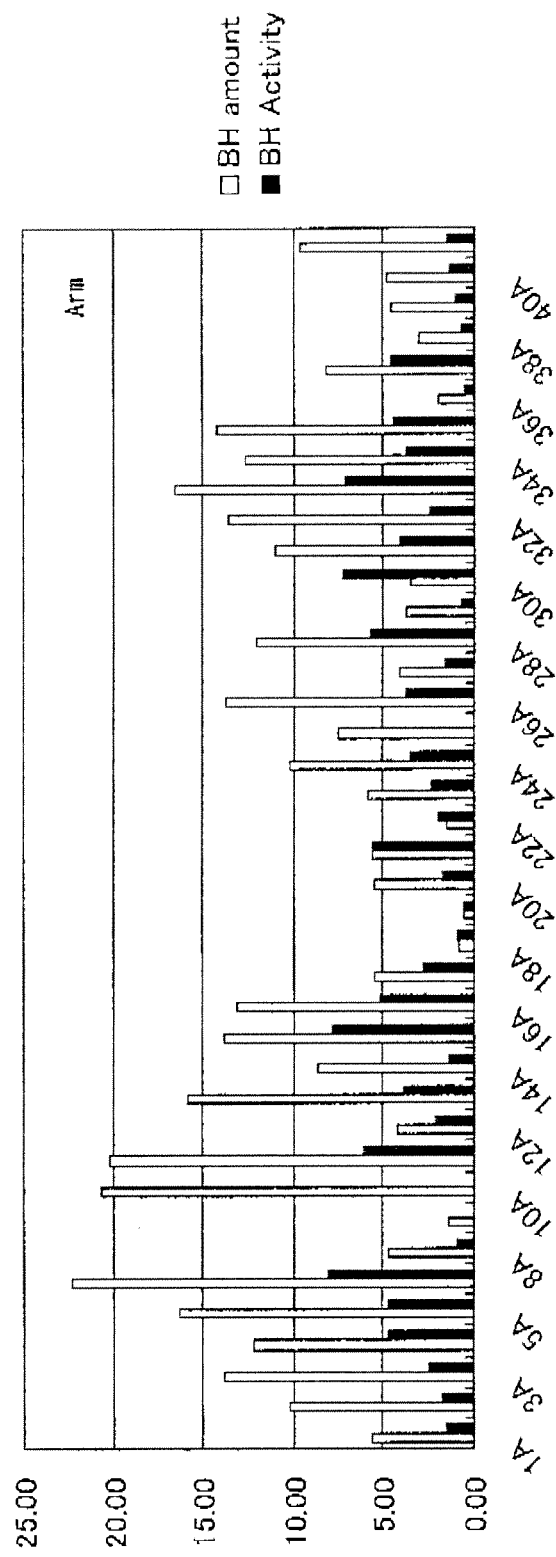
FIG. 3 is a graph indicating the relationship between the amount of bleomycin hydrolase and the enzyme activity thereof in horny layer extracts obtained from human arms. The numbers on the horizontal axis indicate subject identification numbers.
Figure 4:
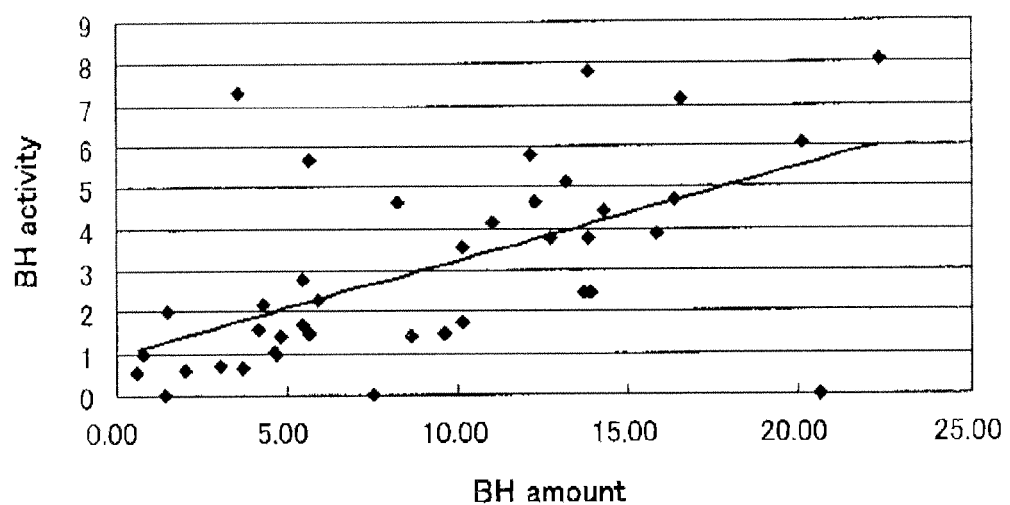
FIG. 4 indicates a first order approximation of the relationship between the amounts and activities of bleomycin hydrolase obtained in FIG. 3 as determined according to the least-squares method.

In this experiment, a study was made of individual differences in the amount and activity of bleomycin hydrolase in human skin and the correlation between the amount and activity of this enzyme. Horny layer extracts were prepared from the skin of 40 female students ranging in age from 20 to 25 years old in accordance with the method described in Experiment 1. The amounts of bleomycin hydrolase in the extracts and the activity thereof were measured in accordance with the method of Kamata, at al. (J. Biol. Chem., Vol. 284, Issue 19, 12829-12836, May 8, 2009). Expression levels were evaluated by western blotting, while aminopeptidase activity of the enzyme was evaluated by measuring the decomposed amount of Cit-β-NA used for the fluorogenic substrate. The results are shown in FIG. 3, and a correlation diagram thereof is shown in FIG. 4. As is clear from the results depicted in FIG. 4, a correlation exists between the amount of bleomycin hydrolase and the activity thereof.

Then, a statistical analysis was carried out on bleomycin hydrolase and various skin parameters for the aforementioned horny layer extracts. In this experiment, the horny layer extracts from 40 subjects were classified into the following two types. After converting the amounts of bleomycin hydrolase determined from the results of western blotting into numerical values with a densitometer, extracts having an amount of bleomycin hydrolase of less than 10 in the case of using a value of "1" as an arbitrary unit and having enzyme activity of less than 1.5 nmol/min/ml were classified as having a low protein level of bleomycin hydrolase and low activity (BH low), while all other extracts were classified as having a high protein level and high activity (BH high).

Figure 5:
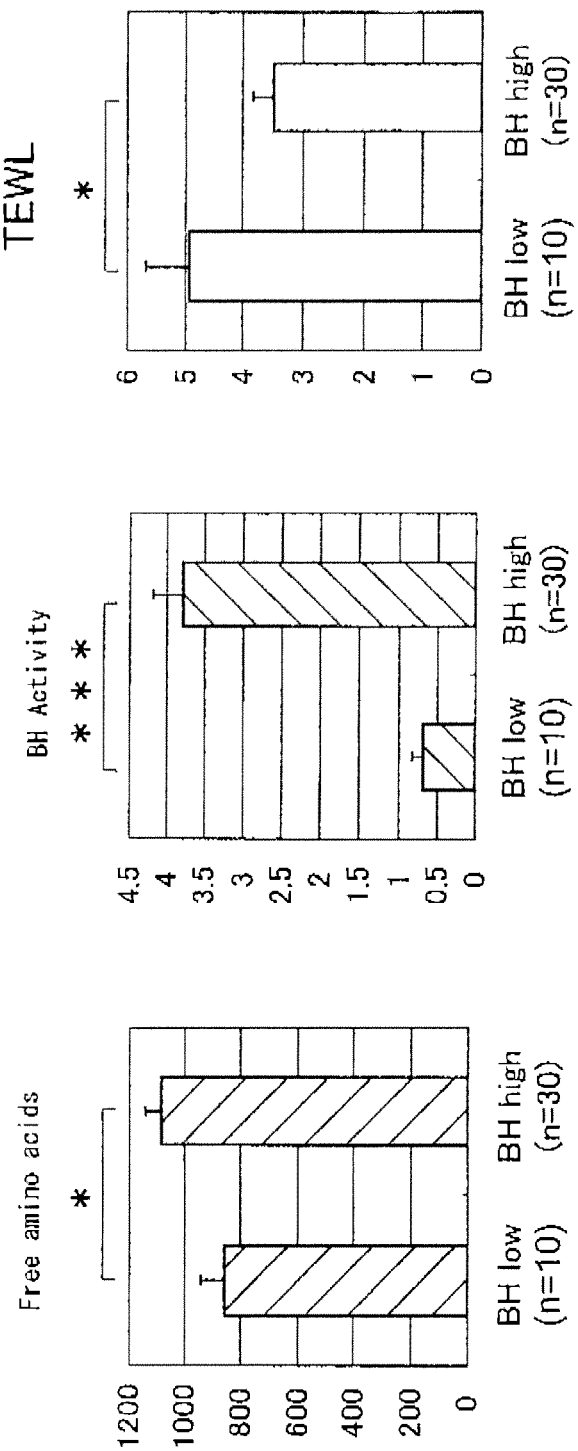
FIG. 5 indicates statistical analyses relating to bleomycin hydrolase present in horny layer extracts obtained from human arms and skin parameters (A: free amino acids, B: activity, C: TEWL). BH low: bleomycin hydrolase level<10, activity<1.5 (nmol/min/ml); BH high: bleomycin hydrolase level≥10, activity≥1.5 (nmol/min/ml).

Free amino acids were measured in accordance with the method of Kamata, et al. (J. Biol. Chem., Vol. 284, Issue 19, 12829-12836, May 8, 2009). More specifically, filaggrin peptide decomposed with calpain I was allowed to react with each extract followed by quantifying the amount of amino groups using Fluorescamine and measuring the amount of free amino acids. The results of measuring free amino acids are shown in FIG. 5A. The units of the vertical axis in FIG. 5A represent the total amount of free amino acids (nmol) in 3 ml of measurement sample.

As was previously described, bleomycin hydrolase activity was evaluated as the aminopeptidase activity of the enzyme by measuring the decomposed amount of Cit-β-NA serving as a fluorogenic substrate. The results of measuring bleomycin hydrolase activity are shown in FIG. 5B. The units of the vertical axis in FIG. 5B represent the decomposed amount of Cit-β-NA (nmol/min/ml).

TEWL levels in the skin of the aforementioned students were measuring using a Vapometer (Delfin Technologies, Ltd., Finland), and were indicated in $g/m^2/h$. The results of measuring TEWL levels are shown in FIG. 5C.

As shown in FIG. 5C, a significant difference in horny layer moisture levels was present between the group having low bleomycin hydrolase activity (2.5 U<) and the high group. Moreover, in the group in which both the amount and activity of this enzyme were low, free amino acid levels were low and TEWL levels were high (FIGS. 5A and 5C).

Although the data is not shown, significant differences in the amounts of NMF and urocanic acid were present between the low free amino acid group (1000<) and the high free amino acid group, while a significant difference in urocanic acid levels was present between the low NMF group (0.8<) and the high NMF group. In addition, significant differences in NMF, lactic acid and urea were present between the low TEWL group (2.5<) and the high TEWL group. When considering that urocanic acid is produced from histidine that is present in large amounts in filaggrin, bleomycin hydrolase can be determined to play an important role in the decomposition of filaggrin.

On the basis of the results of this experiment, both free amino acid levels and barrier function can be determined to decrease significantly in the case of a low absolute amount of bleomycin hydrolase. Although the data is not shown, even in the case of using a horny layer extract derived from the cheek, a proportional relationship was confirmed to exist between the amount of bleomycin hydrolase and barrier function.

Experiment 3

Figure 6:
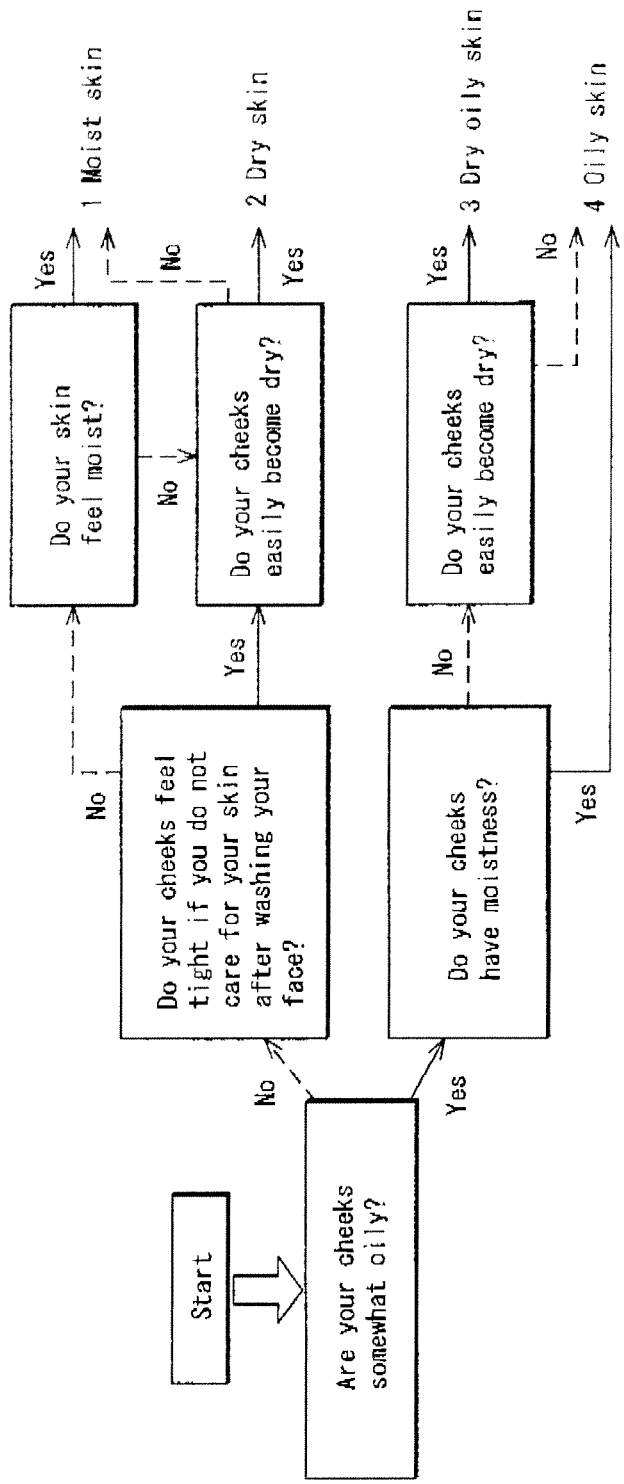
FIG. 6 is a flow chart of a survey used to classify skin.
Figure 7:
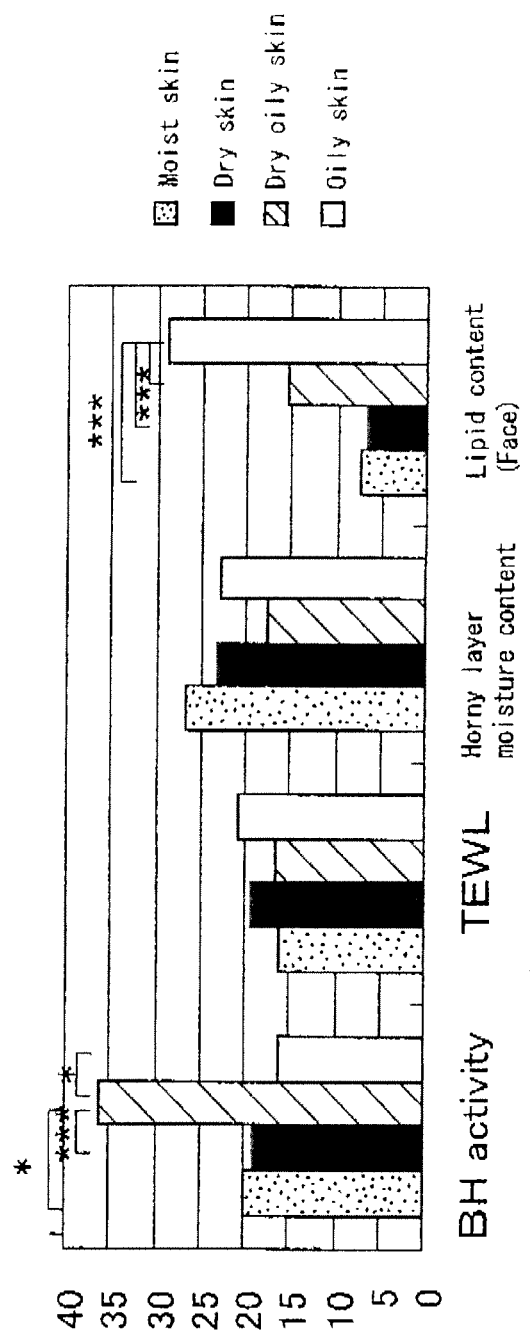
FIG. 7 shows the results of measuring skin parameters of the horny layer obtained from subjects classified according to the flow chart of FIG. 6.

In this experiment, a survey was conducted among the aforementioned female students based on the flow chart shown in FIG. 6, and the skin of the students was classified into one of four categories consisting of moist skin, dry skin, dry oily skip and oily skin. The results of this survey and the correlation with the results for skin parameters measured in the aforementioned Experiment 2 are shown in FIG. 7. On the basis of FIG. 7, bleomycin hydrolase activity of students classified as having oily dry skin was determined to be significantly high.

Experiment 4

In this experiment, a study was made of the localization of bleomycin hydrolase and filaggrin in the skin.

Immunohistochemical Staining

Immunohistochemical staining was carried out according to the method of Kamata, at al. (J. Biol. Chem., Vol. 284, Issue 19, 12829-12836, May 8, 2009). Frozen sections of human skin having a thickness of 5 μm and anti-rat BH IgG were used for the samples. More specifically, human skin specimens were obtained from patients suffering from atopic dermatitis at the Tokyo Medical University after obtaining their informed consent. This study was approved by the Tokyo Medical University Institutional Review Board and a Shiseido Special Subcommittee with respect to human ethics.

Sections of human atopic dermatitis (affected skin and unaffected skin) and normal skin were incubated for 1 hour at room temperature with anti-rat BH IgG and anti-human filaggrin IgG, followed by washing with PBS and further incubating with a fluorescent bound secondary antibody in the form of Alexa Fluor 555 or 488 (Molecular Probes Inc., Eugene, Oreg.). DAPI (4',6'-diamidino-2-phenylindole, Molecular Probes) was used to visualize the nucleus.

The results of tissue staining normal skin are shown in FIG. 8, while the results of comparing skin from a healthy subject (normal skin) and skin from a patient with atopic dermatitis (location of atopic rash) are shown in FIG. 9. As shown in FIG. 9, bleomycin hydrolase was shown to be highly expressed in the upper layer of the epidermis and localized in the same manner as filaggrin. On the other hand, at locations of atopic rash, expression of bleomycin hydrolase and filaggrin were low in comparison with normal skin (FIG. 9).

Quantitative PCR

The expression level of bleomycin hydrolase in keratinocytes was measured by quantitative PCR using the method described below. Measurement was carried out using the Light Cycler 480 (Roche Diagnostics GmbH, Mannheim, Germany), while Light Cycler FastStart DNA Master CYBR Green I was used for the reagent. 0.6 μl aliquots of each of the following bleomycin hydrolase primers and 6.9 μl of water were added to 10 μl of SYBR Green I master mix to bring to a total volume of 20 μl followed by carrying out 45 cycles of PCR consisting of 15 seconds at 95° C., 20 seconds at 55° C. and 20 seconds at 72° C. The results obtained were corrected by comparing with the results for a housekeeping gene in the form of G3PDH.

```
Forward primer:
                                        (SEQ ID NO. 1)
TGTGGTTTGGCTGTGATGTT Reverse primer:
                                        (SEQ ID NO. 2)
GCACCATCCTGATCATCCTT
```

The results of the aforementioned quantitative PCR are shown in FIG. 10. As shown in FIG. 10, bleomycin hydrolase was expressed higher in keratinocytes that had reached confluence, namely differentiated keratinocytes, in comparison with keratinocytes at 80% confluence, namely undifferentiated keratinocytes. In other words, on the basis of the results of this experiment, this enzyme was determined to not be expressed at high levels in basal cells prior to differentiation. The results of this quantitative PCR support the results obtained in the aforementioned tissue staining.

Experiment 5

1) Lucerifase Assay of BH Promoters Using Human Epidermal Keratinocytes

Figure 12:
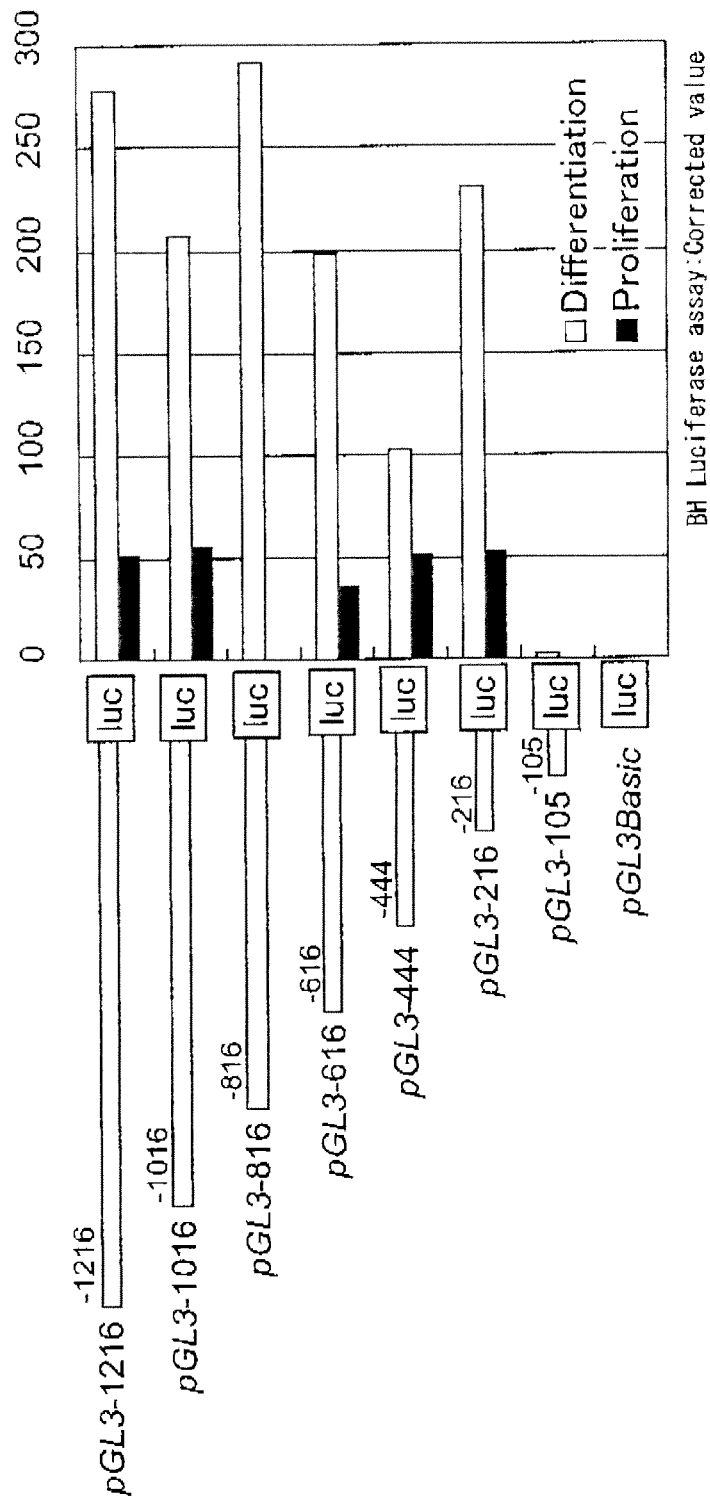
FIG. 12 is a graph indicating the results of a luciferase assay of BH promoters using human epidermal keratinocytes.

Lysis buffer (200 μl) was added to proliferative phase keratinocytes (approx. 80% confluence) or differentiated keratinocytes (after reaching confluence, exposing to air and adding 2 mM calcium followed by continuing to culture for 2 days) to lyse the cells. The Bright-Glo Luciferase Assay System (Promega Co., Madison, Wis., USA) was used for measurement. 20 μl of sample were transferred to a prescribed tube followed by measurement using the Auto Lumat Plus (L89538, Berthold GmbH & Co., KG, Bad Wildbad, Germany). Based on the results shown in FIG. 12, it was determined that in order to express bleomycin hydrolase, the aforementioned transcription regulatory region must have a region extending at least 216 bp downstream from the sequence encoding the enzyme.

2) UV Irradiation of NHEK

RNA was collected by a prescribed method at 3 hours, 24 hours and 48 hours after irradiating with UVB at 30 mJ or 60 mJ (Torex F120S-E-30/DMR, 20 W, Toshiba Medical Supply), and mRNA expression levels of bleomycin hydrolase and calpain were measured by quantitative PCR. As a result, the sample collected 48 hours after irradiating at 30 mJ expressed the highest level of bleomycin hydrolase (FIG. 13).

3) Effect of Cytokines on Bleomycin Expression

Figure 14:
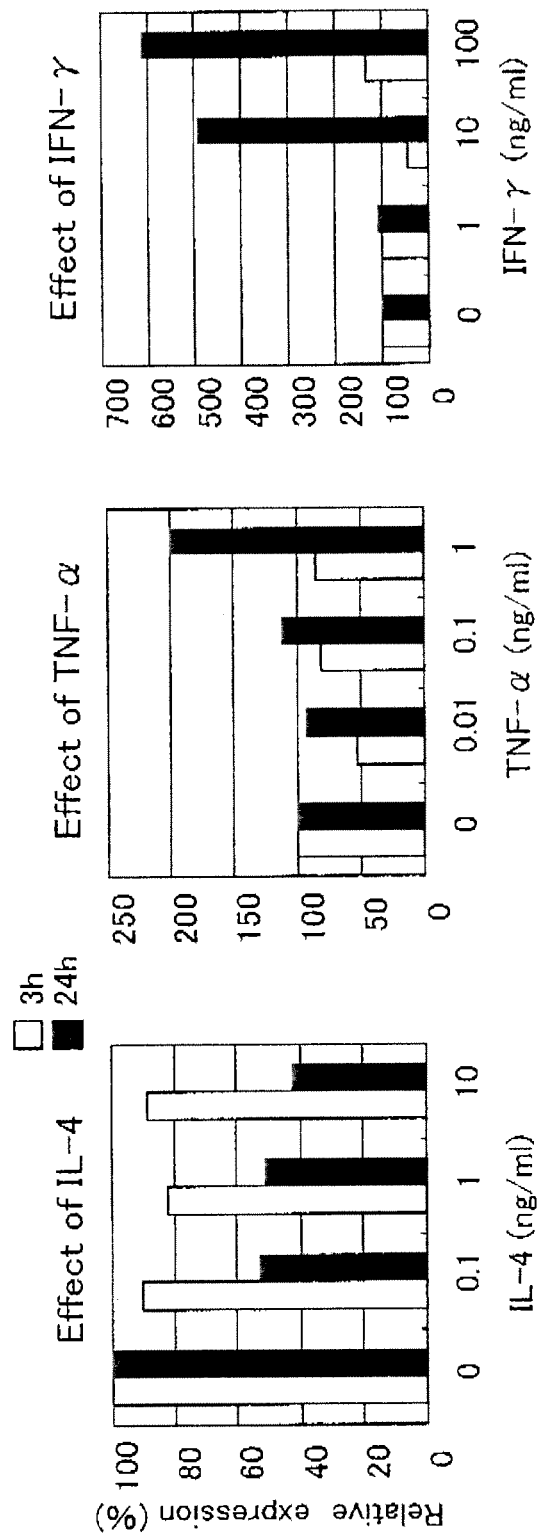
FIG. 14 shows graphs indicating the relationship between the expression levels of bleomycin hydrolase and proteases and UV irradiation in normal human epidermal keratinocytes.

IL-4 (final concentration: 0.1, 1.0 or 10 ng/ml), TNF-α (final concentration: 0.1, 1.0 or 10 ng/ml) and IFN-γ (final concentration: 1.0, 10 or 100 ng/ml) were respectively added to proliferative stage cultured keratinocytes, and after incubating for 24 hours, RNA was collected using Isogen. Expression of bleomycin hydrolase mRNA was measured by quantitative PCR. The results are shown in FIG. 14. Based on the results shown in FIG. 14, interleukin-4 (IL-4), which is a type of Th2 cytokine, was determined to down-regulate expression of bleomycin hydrolase.

Experiment 6

Characterization of Human BH Gene

1) Cloning of BH 5' Flanking Region

The 5' flanking region of BH was amplified based on the nucleotide sequence of human BH gene using the Genome Walker Kit (Clontech, Mountain View, Calif.) in accordance with the manufacturer's protocol by using a gene-specific primer 1 (GSP1) having the sequence 5'-tcctcgagtctgtatcagagcagctaca-3' (SEQ ID NO. 3) and a gene-specific primer 2 (GSP) having the sequence 5'-tgaacacgcgtccgagctgctcatggcg-3' (SEQ ID NO. 4). In brief, primary PCR was carried out using Ex Taq DNA Polymerase (Takara, Shiga, Japan) in the presence of 5% dimethylsulfoxide by using GSP1 and an adapter primer (AP) 1 and using a two-step PCR protocol recommended by the manufacture consisting of 7 cycles of 25 seconds at 94° C. and 4 minutes at 72° C. followed by 32 cycles of 25 seconds at 94° C. and 4 minutes at 67° C., and finally elongation for 4 minutes at 67° C. Next, the primary PCR mixture was diluted and used as a template of secondary PCR amplification using GSP2 and AP2. Secondary PCR was carried out in the same manner as primary PCR with the exception of using 5 cycles instead of 7 cycles for the initial number of cycles and using 20 cycles instead of 32 cycles for the subsequent number of cycles. Continuous 5'-deletion mutants of the 5' flanking region of BH were produced by PCR using the primers shown in FIG. 15. Following amplification, all of the PCR products were cloned in pGEM-T Easy Vector (Promega, Madison, Wis.) followed by sequence determination using the ABI Prism 310 Genetic Analyzer (Applied Biosystems, Foster City, Calif.).

In order to construct a reporter plasmid pGL3-1216/+1, PCR was carried out under the conditions of 30 cycles of initial denaturation for 4 minutes at 94° C., 30 seconds at 94° C. and 1 minute at 72° C. followed by final elongation for 4 minutes at 72° C. using as templates pGEM-T-1216/+1 along with a pair of specific BH primers (5'-ccgggtaccatcagagttccttagaa-3' (SEQ ID NO. 5) and 5'-taaatacgcgttggcgcccacgctgccg-3' (SEQ ID NO. 6)) containing restriction sites KpnI and MluI. The resulting PCR mixture was digested with KpnI and MluI and cloned in pGL3-Basic vector (Promega). Furthermore, the pGL3-Basic vector contains firefly luciferase gene. All of the constructs were prepared using the Qiagen Plasmid Midi Kit (Qiagen, Dusseldorf, Germany).

2) Site-Specific Mutagenesis

Mutagenesis of MZF-1, Sp-1 and IRF-1/2 binding sites was carried out by using the Quick Change Site-Directed Mutagenesis Kit (Stratagene, La Jolla, Calif.) in accordance with the manufacturer's protocol. Primers consisting of 5'-ggaccccgtttcagcctccccgcc-3' (SEQ ID NO. 7) (forward primer of mutant Sp-1 site) and 5'-ggcggggaggct-gaaacggggtcc-3' (SEQ ID NO. 8) (reverse primer of mutant Sp-1 site) were used to produce a deletion mutation in Sp-1. Primers consisting of 5'-gactcagcaacgcggttttgtccctccgc-3' (SEQ ID NO, 9) (forward primer of mutant MZF-1 site) and 5'-gcggagggacaaaaccgcgttgctgagtca-3' (SEQ ID NO. 10) (reverse primer of mutant MZF-1 site) were used for the MZF-1 mutant. Primers consisting of 5'-gccgccgagcctccggcgctcc-3' (SEQ ID NO. 11) (forward primer of mutant IRF-1/2 site) and 5'-ggagcgccggaggctcggcggc-3' (SEQ ID NO. 12) (reverse primer of mutant IRF-1/2 site) were used for the IRF-1/2 mutant.

3) Transfection and Measurement of Promoter Activity

Keratinocytes were cultured in a 12-well tissue culture plate at a density $5 \times 10^4$ cells/well, and were transfected using FuGene HD Transfection reagent (Roche Diagnostics, Basel, Switzerland) and 1 µg aliquots of each construct. All of the cells were simultaneously transfected with pGL4.74 [hRluc-TK] vector (Promega) containing sea pansy (Renilla) luciferase under the control of an HSV-TK promoter for the purpose of correcting transfection efficiency. Unless specifically indicated otherwise, the cells were collected 24 hours after transfection and lysed using the Passive Lysis buffer (Promega) at 250 µl per well. Luciferase activity was analyzed using the Dual Luciferase Reporter Assay System (Promega) and Autolumat Plus Luminometer (Berthold Technologies, Bad Wildbad, Germany). Firefly luciferase activity was standardized based on the sea pansy luciferase activity. Three transfection procedures were carried out independently on each construct, and the results were represented in the form of an average value.

4) Quantitative Real-Time RT-PCR Analysis

The transcription levels of BH and related factors were analyzed by quantitative real-time RT-PCR. Total RNA was extracted from cultured cells using Isogen (Nippon Gene, Tokyo, Japan) in accordance with the manufacturer's protocol. The total RNA was reverse-transcribed to cDNA using SuperScript™ II (Invitrogen, Carlsbad, Calif.). Real-time RT-PCR was carried out with the LightCycler Raid Cycler System using the LightCycler 480 SYBR Green I Master (Roche Diagnostics) in accordance with the manufacturer's protocol. Information relating to the primers used is shown in FIG. 16. Glyceraldehyde 3-phosphate dehydrogenase (GAPDH) was used as a reference gene. Specificity of the amplified fragments was confirmed by quantitative analysis of melting curves using LightCycler analytical software. The amounts of mRNA were standardized based on the mRNA of GAPDH and finally indicated as a ratio to mRNA of an untreated control.

5) siRNA-Based Inhibition of IRF-1 and IRF-2

Cultured keratinocytes were transfected using Lipofectamine RNAi Max (Invitrogen, Carlsbad, Calif.) with 40 nM siIRF-1, siIRF-2 and siControl A (Santa Cruz Biotechnology, Santa Cruz, Calif.) in accordance with the manufacturer's protocol. The cells were then cultured for 24 hours in antibody-free media, followed by extracting the total RNA and analyzing by real-time RT-PCR in the manner previously described.

6) Electrophoretic Mobility Shift Analysis (EMSA)

Double-stranded oligonucleotide probes were prepared by annealing single-stranded biotinated oligonucleotides with single-stranded unlabeled oligonucleotides (FIG. 17). Nuclear extraction and EMSA were carried out using a Nuclear Extraction Kit and EMSA Gel Shift Kit (Panomics, Santa Clara, Calif.). The nuclear extracts (4 µg) were incubated for 30 minutes at 15° C. with 1× binding buffer, 1 µg of Poly[d(IC)] and biotinated probes (50 pmol) corresponding to the MZF-1, Sp-1, IRF-1/2 and GATA-1 binding sites. In order to carry out a competitive assay, a two-fold excess amount of unlabeled probe was added to binding reaction prior to addition of the biotinated probes. These incubation mixtures were then electrophoresed with 0.5×TBE buffer in 8% polyacrylamide gel followed by transfer to a Biodyne B Nylon membrane (Pall, Port Washington, N.Y.). The bands were visualized by using the chemiluminescence detection kit provided in the EMSA Gel Shift Kit.

7) Results

Isolation and Characterization of Human BH Gene Promoters

A large number of putative transcription factor binding sites have been determined to be present within the 5' flanking region of human BH based on the results of a search using the Genome Net MOTIF program (FIG. 16A). In particular, since sequences showing close coincidence with consensus sequences recognized by MZF-1, Sp-1, IRF-1/2 and GATA-1/2 are present in a region extending from −216 to +1 near the locations of transcription initiation sites, these transcription factors were suggested to be involved in the regulation of BH promoter activity. More precisely, a deletion analysis was carried out to determine BH promoter regions (FIG. 18B). The highest level of luciferase activity was detected in differentiated keratinocytes transfected with pGL3-816. However, the relative luciferase activity of the deletion plasmids remained high until deletion proceeded to pGL3-216. Among the constructs, the plasmid containing the fragment extending from −444 to +1 (indicated as pGL3-444) demonstrated significantly lower activity in the cultured keratinocytes, and upstream suppressor activity was suggested to be present in the −616 to −444 region. Since these results demonstrated that the region from −216 to −1 contains the minimal promoter for BH gene transcription, the nucleotide sequence thereof is shown in FIG. 18C. Since this sequence did not contain a TATA or CCAAT box, it was suggested to possess housekeeping properties of this gene. On the other hand, several transcription factor binding sites, such as MZF-1, Sp-1, IRF-1/2 and GATA-1/2, were present in this core promoter region.

Identification of Latent Cis-Acting Element Involved in BH Gene Regulation

Figure 19:
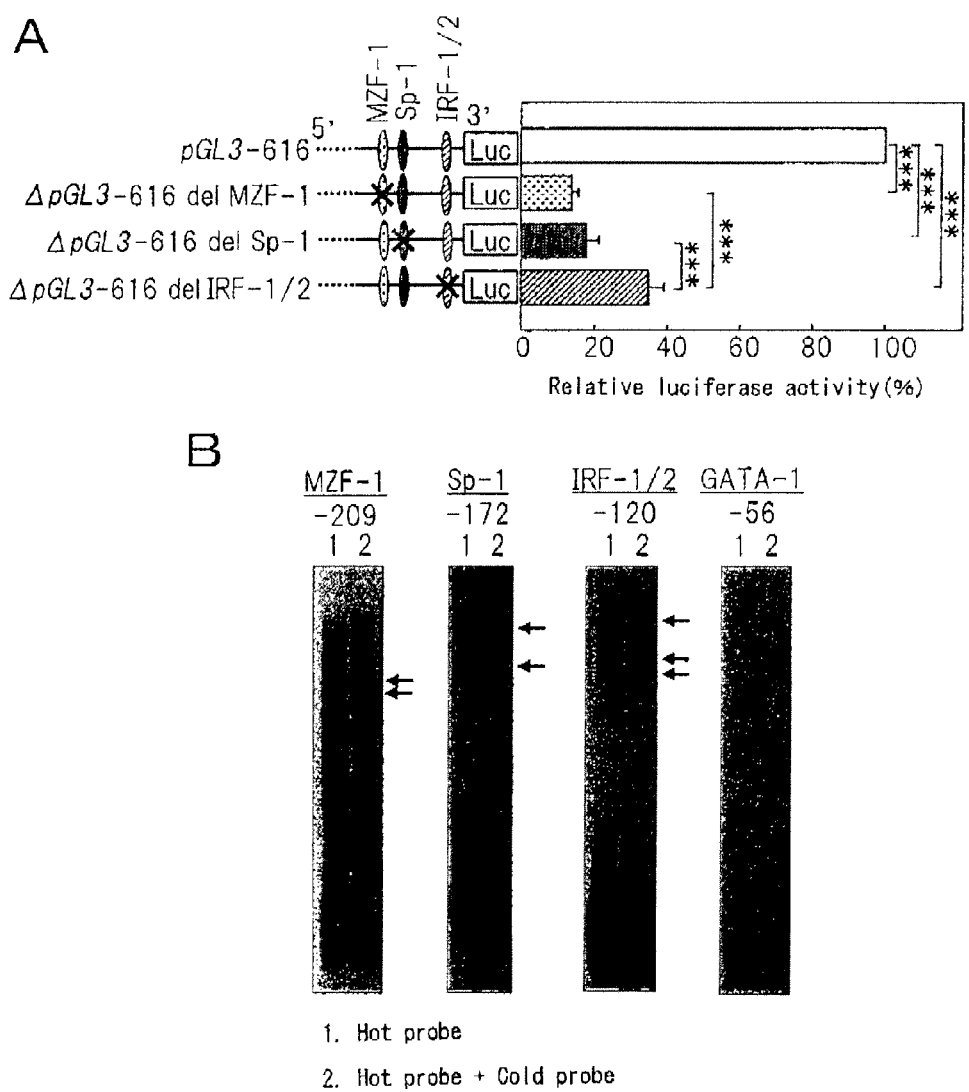
FIG. 19A indicates characterization of transcription factor binding sites in BH promoters by site-specific mutagenesis, a schematic diagram of deletion constructs of putative transcription factor binding sites, and the luciferase activity thereof in cultured keratinocytes. Site-specific mutagenesis was carried out in constructs spanning the nucleotide sequence of the region from −616 to +1.
FIG. 19B indicates binding of MZF-1, Sp-1, GATA-1 or IRF-1/2 to the cis-acting element of BH promoters. The experiment was carried out with an electrophoretic mobility shift assay (EMSA) using a nuclear extract from cultured keratinocytes and a biotinated double-stranded oligonucleotide probe containing putative transcription factor binding site MZF-1, Sp-1, GATA-1 or IRF-1/2. Lane 1 indicates the binding profile of the biotinated probe in the nuclear extract, while lane 2 indicates the binding profile of the biotinated probe after competing with a non-labeled probe present in an excess amount equal to twice the amount of the biotinated probe.

A new series of deletion mutants was constructed targeted at each cis-acting element to determine the latent cis-acting element of the minimal promoter involved in regulating transcription of BH gene expression. Promoter activity was greatly down-regulated in the case of deleting the MZF-1, Sp-1 and IRF-1/2 binding sites (FIG. 19A).

Moreover, en investigation was conducted as to whether or not these transcription factors are actually able to bind to each of the putative binding sites. Therefore, an electrophoretic mobility shift assay (EMSA) was carried out using a nuclear extract from cultured keratinocytes along with double-stranded oligonucleotide probes containing the MZF-1, Sp-1, GATA-1 or IRF-1/2 binding site. As shown in FIG. 19B, although Sp-1, MZF-1 and IRF-1/2 bound to the target site corresponding to BH promoter, GATA-1/2 did not bind. These results indicate that these binding sites of the promoter region extending from −216 to −105 bp are essential for the cis-acting element for BH transcription.

Cytokine-Mediated Regulation of BH Gene Expression

Since BH is an NMF-generating enzyme, it has the potential to be involved in the pathophysiology of AD. Accordingly, an investigation was made of the effects of cytokines Th1, Th2 and Th17 on EH gene expression. FIG. 20A indicates that the Th1 cytokine, IFN-γ, down-regulated expression of BH mRNA in a dose-dependent manner in proliferative keratinocytes. On the other hand, cytokines Th2 and Th17 did not demonstrate any significant effects whatsoever on BH expression. Similar results were obtained with differentiated keratinocytes (data not shown). A promoter assay was carried out in order to determine the role of IFN-γ in regulation of BH gene expression, and response elements were specified. As shown in FIG. 20B, IFN-γ down-regulated BH promoter activity in proliferative keratinocytes transfected with pGL3-BH-616 containing an IRF-1/2 binding sequence between −131 and −120. Following deletion of this sequence, IFN-γ no longer inhibited BH promoter activity (FIG. 20B). In addition, IRF-1 and IRF-2 gene expression was inhibited using small interfering RNA (siRNA) in order to determine whether or not IRF-1/2 is an essential mediator of IFN-γ-induced down-regulation of BH. IFN-γ activity was significantly inhibited in cultured keratinocytes transfected with either IRF-1 or IRF-2 siRNA (40 nM) (FIG. 20C). These results strongly suggest that the IRF-1/2 binding sequence is essential for IFN-γ-induced down-regulation of BH gene expression.

Expression of BH and Related Factors in Cultured Keratinocytes

Figure 21:
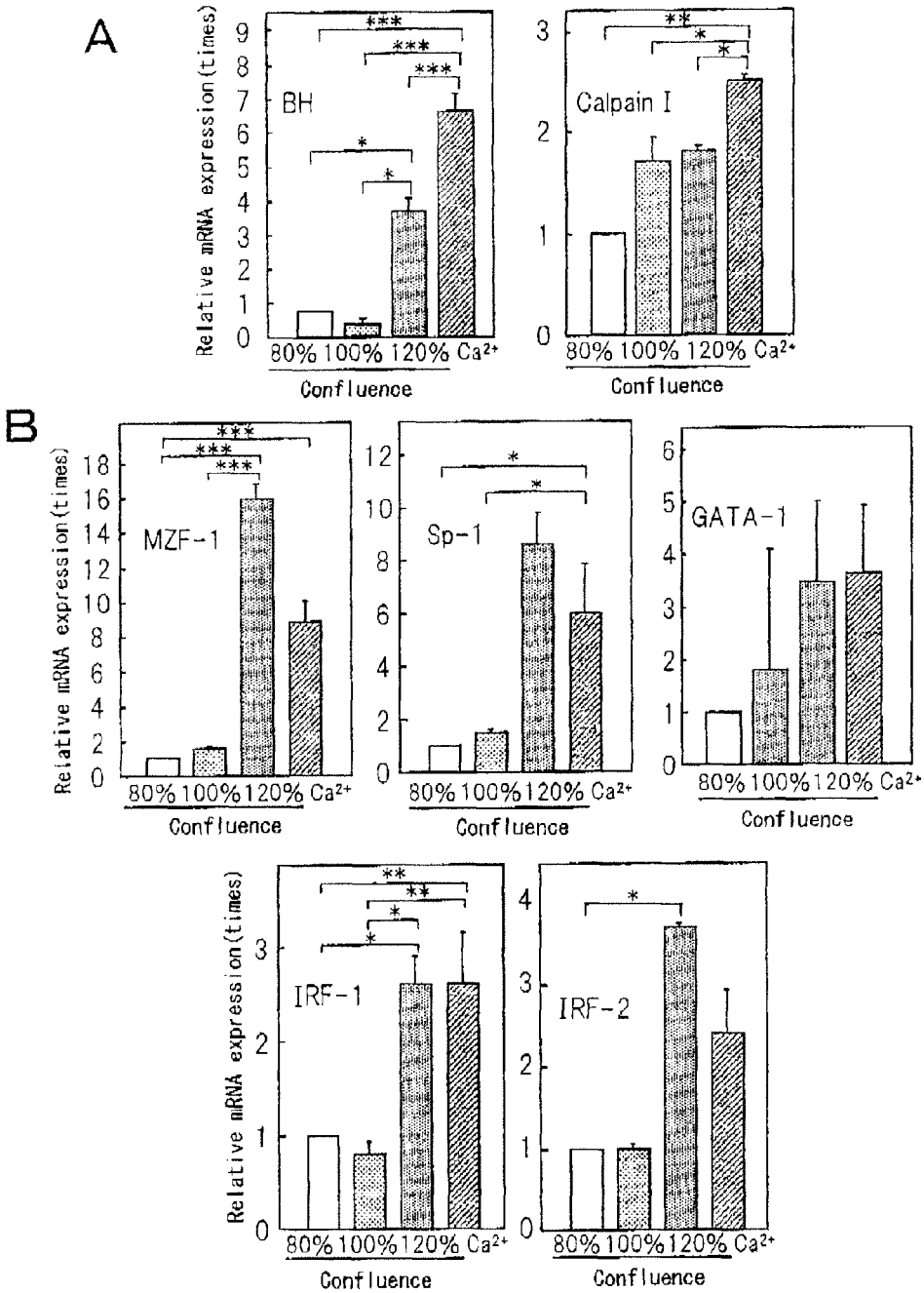
FIG. 21A shows the results of an expression analysis of BH, calpain and putative transcription factors in proliferative or differentiated cells by real-time PCR to investigate the mechanism of transcription control in the epidermis.
FIG. 21B shows the results of an analysis of the expression patterns of transcription factors MZF-1, Sp-1, GATA-1, IRF-1 and IRF-2 in cultured keratinocytes.

The expression of BH, calpain-1 and putative expression factors in proliferative and differentiated cells was analyzed by real-time PCR in order to investigate the mechanism of transcription regulation in the epidermis. As shown in FIG. 21A, BH mRNA was up-regulated in differentiated keratinocytes, such as in those 2 days after the confluent stage (3.6 times) and those cultured at a high calcium concentration (8.6 times), in comparison with proliferative keratinocytes. These results coincide with the promoter assay data (FIG. 18B). Similar results were also obtained with respect to calpain I (roughly 2.5-fold increase in up-regulation). In addition, an investigation was made of expression vectors of various transcription factors such as MZF-1, Sp-1, GATA-1, IRF-1 and IRF-2 in proliferative keratinocytes. As shown in FIG. 21B, these transcription factors were up-regulated in differentiated keratinocytes in line with BH expression. However, expression of GATA-1 mRNA was significantly lower in comparison with other factors (<1/32). GATA-1 is thought not to play an important role in keratinocytes. Accordingly, BH is suggested to be synthesized in a differentiation-dependent manner mediated by MZF-1 and Sp-1. The fact to that IRF-1 and IRF-2 are also up-regulated by differentiation stimuli indicates that BH expression is extremely sensitive to IFN-γ.

Figure 22:
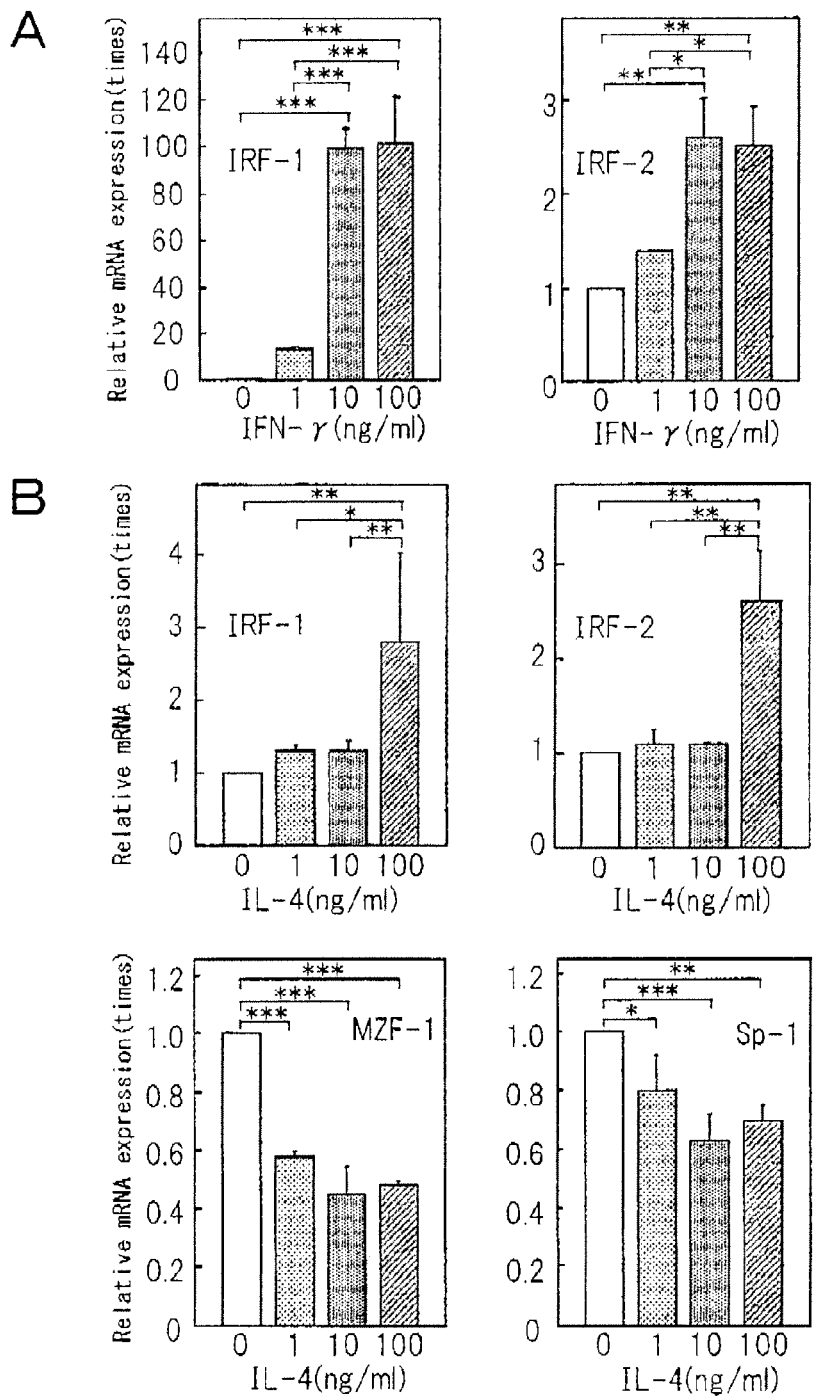
FIG. 22A indicates the effects of IFN-γ on expression of putative transcription factors IRF-1 and IRF-2.
FIG. 22B indicates the effects of IL-4 on expression of putative transcription factors IRF-1, IRF-2, MZF-1 and Sp-1.

Effects of Cytokines Th1 and Th2 on Expression of Putative Transcription Factors An investigation was made of the cytokine-dependent regulation of these transcription factors. FIG. 22A indicates that IFN-γ strongly up-regulates expression of IRF-1 mRNA in a dose-dependent manner. Similarly, expression of IRF-2 was up-regulated in the presence of IFN-γ. In contrast, expression of IRF-1 and IRF-2 was significantly enhanced only in the presence of IL-4 at 100 ng/ml (FIG. 22B). It is interesting to note that both MZF-1 and Sp-1 were most effectively down-regulated in the presence of IL-4 at 10 ng/ml (FIG. 22C). These results suggest that expression of BH is regulated directly and indirectly by cytokines Th1 and Th2, respectively.

Down-Regulation of BH in Atopic Dermatitis Skin

Although loss-of-function mutations of FLG are related to the mechanism of occurrence of AD, there is the possibility of this being related not to a gene deletion, but rather to a disorder in the decomposition pathway or the pathology of AD. Consequently, an investigation was next made of the localization of BH and filaggrin in affected skin and unaffected skin of AD patients along with BH activity at those locations. In normal skin, double staining with anti-BH antibody and anti-filaggrin antibody demonstrated simultaneous localization of BH and filaggrin in the upper epidermis, and particularly in the granular layer, as previously reported (FIG. 23A). At a higher magnification, although BH was clearly indicated to be localized from the granular layer to the horny layer, filaggrin was limited to granular cells. In contrast, BH expression decreased dramatically in the affected skin and unaffected skin of AD patients observed in this study (n=7). All of these results indicated that, even though significant staining was detected at all times, comparatively weak filaggrin staining was indicated (FIG. 23A). In addition to immunohistochemistry, BH activity was measured in horny cell extracts from tape peeling samples obtained from 18 AD patients and 30 healthy volunteers. The extracts obtained from affected skin and unaffected skin of the AD patients demonstrated substantially lower BH activity than that of the healthy volunteers (27.1% and 8.8% lower, respectively) (FIG. 28B). These results demonstrated that BH is simultaneously localized with filaggrin, and that the activity thereof is dramatically decreased in the skin of patients suffering from AD.

Discussion

In this study, the regulatory mechanism of BH gene expression was examined by cloning and functional characterization of the promoter region. A region important for BH promoter activity was identified to be present in a region located −216 bp upstream by promoter analysis (FIG. 18B). In this region, putative MZF-1 and Sp-1 binding sites demonstrated a significant effect on BH promoter activity (FIGS. 18C and 19A). It is interesting to note that Sp-1 and MZF-1 have also been reported to be involved in the regulation of PAD1 that is an important enzyme for initiation of filaggrin decomposition. Sp-1 is a typical member of the Sp/Kruppel-like family of zinc finger proteins that function as transcription factors in mammalian cells. It is thought to be involved in nearly all aspects of cell function, including proliferation, apoptosis, differentiation and neoplastic transformation. In human epidermis, Sp-1 is an important regulatory factor of genes that participate in epidermal differentiation, including the involucrin, loricrin, transglutaminase, and PAD1, PAD2 and PAD3 genes. MZF-1 is a transcription factor that belongs to the Krupple family of zinc finger proteins, and is expressed in differentiated totipotent hematopoietic cells and bone marrow progenitor cells. However, the function of MZF-1 during transcription regulation in mammalian epidermis has not been reported. MZF-1, Sp-1 and BH were found to be simultaneously up-regulated in differentiated keratinocytes in comparison with proliferative keratinocytes (FIG. 21B), indicating the role of BH in differentiation rather than housekeeping. These results clearly indicated that these transcription factors function as activating factors for basic regulation of transcription of BH during final differentiation of keratinocytes.

On the other hand, an investigation of cis-acting elements further defined the IRF-1/2 binding sites within this region. The IRFs were confirmed to bind directly to the BH promoter region by using EMSA (FIG. 19B). Site-specific mutagenesis of this binding region brought about a significant decrease in BH promoter activity (FIG. 13A). Consequently, IRF-1/2 transcription factors are also most likely required for minimal promoter activity of the BH gene under basic conditions. The IRF family consists of a group of transcription factors, and at present, nine IRF members (IRF-1 through IRF-9) have been identified in various cell types and tissues. These IRF molecules play a role in antiviral defense, immune response/regulation and cell growth regulation when stimulated by IFN-α, IFN-β and IFN-γ. IRF-1 and IRF-2 have been demonstrated to function as agonists and antagonists involved in the regulation of numerous IFN-γ-induced genes. It is interesting to note that IFN-γ remarkably decreased expression of BH mRNA (FIGS. 20A and 20B). Knockdown and site-specific mutagenic analyses confirmed that IRF-1/2 binding sites are involved in IFN-γ-mediated inhibition of BH expression (FIGS. 20B and 20C). These results clearly indicate that IRF-1/2 are mediators of IFN-γ-mediated down-regulation of BH gene in human keratinocytes. On the other hand, the Th2 cytokines of IL-4 and IL-13 did not demonstrate any direct action whatsoever during incubation for 24 hours (FIG. 20A). However, these Th2 cytokines significantly inhibited expression of activator molecules in the form of MZF-1 and Sp-1. Accordingly, it is reasonable to think that Th2 cytokines down-regulate expression of BH.

In addition, BH was shown to be dramatically down-regulated in affected and unaffected AD skin (FIGS. 23A and 23B). Although filaggrin mutation is a primary risk factor for diseases related to barrier disorders such as AD, mutation analyses indicated that this mutation accounts for less than 50% of the incidences of these diseases in Ireland and no more than 20% of the incidences in Japan. Defective synthesis of filaggrin as well as disorders associated with filaggrin decomposition are hypothesized to be involved in a breakdown of barrier function. It is clear that decreased levels of NMF bring about dry skin, and that this promotes a breakdown of the skin barrier. AD is well known to be a Th2-polarized disease. However, recent reports have suggested that Th1 cytokines also play a role in AD. For example, "intrinsic AD" is immunologically characterized by low expression levels of IL-4, IL-5 and IL-13 and a high expression level of IFN-γ. In addition, a shift from Th1 to Th2 occurs during a transition from the acute phase to the chronic phase of AD skin. These results also indicate the possibility that IFN-γ may play a more important role than was previously thought.

In conclusion, these results indicate that BH transcription in human epidermis is regulated by two modes of regulation. The first pathway is under the control of final keratinocyte differentiation, while the other pathway is dependent on cytokines Th1 and Th2. Since these pathways are interrelated, the balance there between is likely to easily shift towards down-regulation of BH expression. Since a decrease in BH brings about a shortage of NMF, this leads to dry skin and eventually a subsequent breakdown of barrier function in response thereto. These results provide novel findings regarding the regulation of BH and the mechanism of occurrence of AD.

The invention claimed is:

1. A method for screening and evaluating ameliorants of dry skin caused by atopic dermatitis in a human subject, comprising: evaluating a candidate drug as being an ameliorant of dry skin caused by atopic dermatitis in the case the candidate drug significantly increases expression and/or activity of bleomycin hydrolase in comparison with a control drug in human cells, wherein expression and/or activity of bleomycin hydrolase is judged to have increased significantly in the case the transcription activity of a gene that encodes bleomycin hydrolase has increased significantly in comparison with that of a control and wherein the transcription activity is judged to have increased significantly in the case binding activity of transcription factors IRF-1, IRF-2, MZF-1, Sp-1 and/or GATA-1 to the transcription regulatory region of a gene that encodes bleomycin hydrolase has increased significantly in comparison with that of a control.

* * * * *